(12) United States Patent
Efimov et al.

(10) Patent No.: US 10,875,871 B2
(45) Date of Patent: Dec. 29, 2020

(54) PHOTOSENSITIZER

(71) Applicant: Tampereen Korkeakoulusäätiö sr, Tampereen Yliopisto (FI)

(72) Inventors: Alexander Efimov, Tampere (FI); George Lijo, Tampere (FI); Ville Santala, Tampere (FI)

(73) Assignee: Tampereen korkeakoulusäätiö sr, Tampereen Yliopisto (FI)

( * ) Notice: Subject to any disclaimer, the term of this patent is extended or adjusted under 35 U.S.C. 154(b) by 0 days.

(21) Appl. No.: 16/349,893

(22) PCT Filed: Nov. 9, 2017

(86) PCT No.: PCT/FI2017/050775
§ 371 (c)(1),
(2) Date: May 14, 2019

(87) PCT Pub. No.: WO2018/091774
PCT Pub. Date: May 24, 2018

(65) Prior Publication Data
US 2019/0337958 A1 Nov. 7, 2019

(30) Foreign Application Priority Data

Nov. 17, 2016 (FI) .................................. 20165867

(51) Int. Cl.
| | |
|---|---|
| *C07D 487/22* | (2006.01) |
| *A01N 43/90* | (2006.01) |
| *A61L 2/08* | (2006.01) |
| *A61L 2/232* | (2006.01) |
| *C07F 3/06* | (2006.01) |

(52) U.S. Cl.
CPC ........... *C07D 487/22* (2013.01); *A01N 43/90* (2013.01); *A61L 2/088* (2013.01); *A61L 2/232* (2013.01); *C07F 3/06* (2013.01)

(58) Field of Classification Search
CPC ....... C07D 487/22; A01N 43/90; A61L 2/088; A61L 2/232; C07F 3/06
USPC ...................................................... 540/145
See application file for complete search history.

(56) References Cited

U.S. PATENT DOCUMENTS

| | | | |
|---|---|---|---|
| 2,211,947 A | 8/1940 | Isidor Morris Heilbron et al. | |
| 2,277,588 A | 3/1942 | Hulton et al. | |
| 2,277,628 A | 3/1942 | Flower et al. | |
| 7,749,991 B2* | 7/2010 | Roncucci | C07C 255/51 514/185 |
| 2007/0155961 A1* | 7/2007 | Gessner | C07D 487/22 540/124 |
| 2012/0068123 A1* | 3/2012 | Sundarraj | B82Y 10/00 252/506 |

FOREIGN PATENT DOCUMENTS

| | | |
|---|---|---|
| CN | 103370642 A | 10/2013 |
| EP | 1164135 A1 | 12/2001 |
| EP | 1356813 A1 | 10/2003 |
| GB | 521749 A | 3/1940 |
| GB | 522293 A | 6/1940 |
| WO | 02096913 A1 | 12/2002 |
| WO | 2007000472 A1 | 1/2007 |
| WO | 2007000473 A1 | 1/2007 |
| WO | WO-2017064243 A1 * | 4/2017 ......... G01N 27/4141 |

OTHER PUBLICATIONS

George; Dyes and Pigments 147 (2017) 334-342. (Year: 2017).*
George; Journal of Inorganic Biochemistry 2018, 183, 94-100. (Year: 2018).*
Grammatikova; J. Mater. Chem. B, 2019, 7, 4379-4384. (Year: 2019).*
Haworth; J. Chem. Soc., 1945, 409-412. (Year: 1945).*
Osifeko; Journal of Photochemistry and Photobiology A Chemistry 2015, 301, 47-54. (Year: 2015).*
International Preliminary Report on Patentability, Chapter II, Application PCT/FI2017/050775, dated Jan. 31, 2019, 6 Pages. (Year: 2019).*
Jiang; Journal of Pharmaceutical and Biomedical Analysis 2014, 87, 98-104. (Year: 2014).*
Kuzyniak; Photodiagnosis and Photodynamic Therapy 2016, 13, 148-157. (Year: 2016).*
Mantareva; Bioorganic & Medicinal Chemistry 2007, 15, 4829-4835. (Year: 2007).*
International Search Report, Application No. PCT/FI2017/050775, dated Mar. 13, 2018, 4 pages.
European Patent Office, Supplementary European Search Report, Application No. 17871183.4, dated Jun. 30, 2020, 11 Pages.
Lijo et al, "Photodynamic self-disinfecting surface using pyridinium phthalocyanine". Dyes and Pigments. Elsevier applied science publishers. vol. 147. Aug. 17, 2017. ISSN: 0143-7208, DOI: 10.1016/J.DYEPIG.2017.08.021, pp. 334-342, 9 Pages.
Donzello et al, "Zinc(II) complexes of tetrakis-(6,7-quinoxalino)porphyrazine bearing externally appended 2-pyridyl rings: Synthesis, UV-visible spectralbehavior and photoactivity for singlet oxygen generation". Journal of Porphyrins and phthalocyanines. vol. 18. No. 1. Oct. 11, 2014, ISSN 1088-4246, DOI: 10.1142/S1088424614500874, pp. 1042-1050, 9 Pages.

* cited by examiner

*Primary Examiner* — Daniel R Carcanague
(74) *Attorney, Agent, or Firm* — Ziegler IP Law Group, LLC

(57) ABSTRACT

The present application relates to a phthalocyanine, to a method for preparing the phthalocyanine, and to an object coated or impregnated with the phthalocyanine. The present application also relates to a method for providing reactive oxygen species, and to a method for disinfecting materials, including providing reactive oxygen species to the material to disinfect the material by oxidative action.

24 Claims, 8 Drawing Sheets

PHOTOSENSITIZER

FIELD OF THE APPLICATION

The aspects of the disclosed embodiments relate to photosensitizers comprising a phthalocyanine, methods for preparing thereof, and to objects coated or impregnated with the phthalocyanine. The aspects of the disclosed embodiments also relate to methods for providing reactive oxygen species, and to methods for disinfecting materials and to methods of phototodynamic therapy.

BACKGROUND

Nosocomial or healthcare associated infections (HAI) account for the major source of transmission of infectious disease. Contaminated surfaces, air and water play an important role in the spread of microbes. These microbes tend to form biofilms and are resistant to antibiotic treatment. Moreover the emergence of drug resistant bacteria is another threat. Photodynamic antimicrobial chemotherapy (PACT) is found to be effective against the spread of drug resistant bacteria and biofilms. The method involves the use of photosensitizers in the presence of light to inactivate the pathogenic microbes by oxidative stress induced with the help of reactive oxygen species (ROS) such as singlet oxygen.

SUMMARY

A novel type of photosensitizer agent comprising a phthalocyanine was discovered, which agent exhibited efficient photosensitizing properties.

One embodiment provides a phthalocyanine of Formula I:

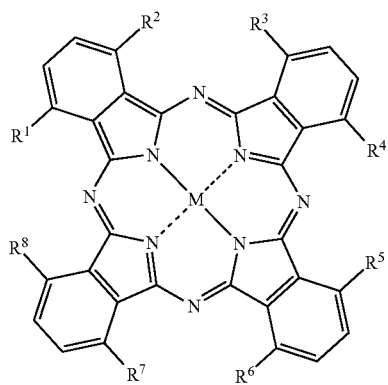

Formula I wherein M is a metal ion or two hydrogen atoms,
and wherein the substituent pairs $R^1$ and $R^2$, $R^3$ and $R^4$, $R^5$ and $R^6$, and $R^7$ and $R^8$, independently of the other substituent pairs, are
a hydrogen, and
the other substituent is the same in all the substituent pairs and is selected from

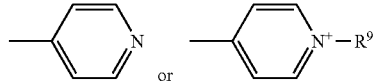

wherein $R^9$ is a C1-C18 alkyl.

One embodiment provides an object coated or impregnated with the phthalocyanine.

One embodiment provides a method for providing reactive oxygen species, the method comprising
providing the phthalocyanine or the object, and
irradiating the phthalocyanine or the object with light,
to obtain reactive oxygen species.

One embodiment provides a method for method for inactivating micro-organisms, comprising providing reactive oxygen species with the above method to inactivate the micro-organisms by oxidative action.

The main embodiments are characterized in the independent claims. Various embodiments are disclosed in the dependent claims. The embodiments recited in the claims and in the specification are mutually freely combinable unless otherwise explicitly stated.

The materials and methods disclosed herein may be used against microbes, especially pathogens. In general the phthalocyanine of the embodiments provides efficacy against many types of pathogens simultaneously, including viruses, fungi and bacteria. It also provides efficacy against undetected and unculturable pathogens, against biofilms, moulds and multi-drug resistant pathogens, and against Hospital Acquired Infections and "superbugs".

The materials and methods also provide a safe actions against the microbes, such as prevention of resistivity in bacteria and control of super bacteria, and reduced environment pollution.

The action provided by the materials and methods is simple. Just exposure to light for 1-2 h is enough for disinfection. No thermal or chemical treatment is needed, which is advantageous because in many places on Earth there is simply no possibility to boil water. The materials are suitable for large surfaces, such as cloths, carpets, seats, walls and the like. The above mentioned advantages have been confirmed in laboratories.

It was also found out that even regular indoor light, such as consumer LED lamps, were useful to obtain the effect with the present materials. This is very beneficial as an inexpensive, economical and long-lasting light source, which is advantageous especially for broad use of photodynamic antimicrobial chemotherapy.

The phthalocyanines are stable and durable. They maintain their activity for a long time, and they do not fade out but remain in the target, such as on the surface of an object or impregnated in the materials of the object.

DETAILED DESCRIPTION

Figure 1:
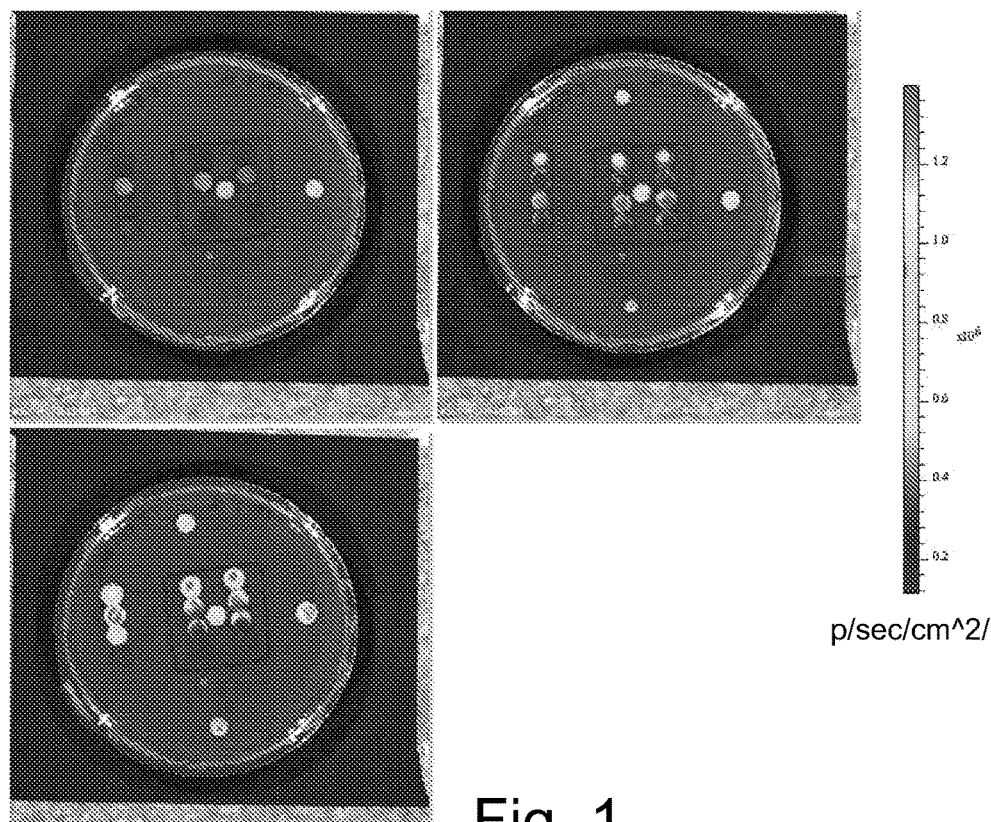
FIG. 1 shows a screening test with *E. coli* βBAV1C-T5-lux

The present application discloses a phthalocyanine dye, which has four pyridyl substituents in its alpha-phthalo positions and methods for preparation thereof. The phthalocyanine may be present either as a free base or as a metal complex, such as a Zn complex, and the pyridyl substituent may be present either as a pyridine or as its N-alkylated derivative.

In general the phthalocyanine having the four pyridyl substituents may be represented with the general formula I:

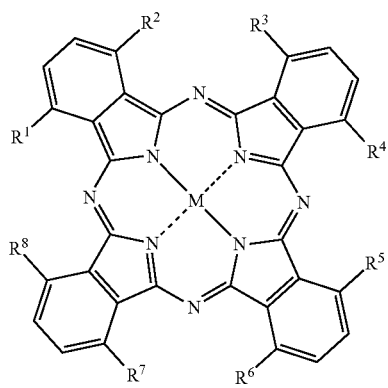

Formula I wherein the substituent pairs $R^1$ and $R^2$, $R^3$ and $R^4$, $R^5$ and $R^6$, and $R^7$ and $R^8$, independently of the other substituent pairs, are
  a hydrogen, and
  the other substituent is the same in all the substituent pairs and is selected from

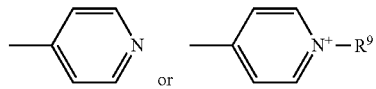

or wherein $R^9$ is a C1-C18 alkyl.

M may be a metal ion or two hydrogen atoms. M may be selected from Zn, Mg, Al, Cu, Co, Mn, Fe, Pt, Pd, Si, P, Sn, Ru, Ag, Au, Ir, Ni, Cd, Hg, U, Li, Na, K, Be, B, Ti, V, Cr, Ga, Ge, As, Y, Mo, Rh, In, Sb, Ba, W, Os, Re, Tl, Pb, and Bi. In one specific example the M is Zn.

There are four R substituents in the molecule, one per phthalo ring, with direct C—C bond between phthalocyanine and pyridine, at the positions marked $R^1$-$R^8$. In one embodiment the substituent is pyridine. In one embodiment the substituent is N-alkylated pyridine.

$R^9$ may be a C1-C18 alkyl, such as methyl, ethyl, propyl, butyl, pentyl, hexyl, heptyl, octyl, nonyl, decyl, undecyl or dodecyl. In one embodiment $R^9$ is a $C_1$-$C_{12}$ alkyl. In one embodiment $R^9$ is a $C_1$-$C_{10}$ alkyl. In one embodiment $R^9$ is a $C_1$-$C_8$ alkyl. In one embodiment $R^9$ is a $C_1$-$C_6$ alkyl. In one embodiment $R^9$ is a $C_2$-$C_{12}$ alkyl. In one embodiment $R^9$ is a $C_2$-$C_{10}$ alkyl. In one embodiment $R^9$ is a $C_2$-$C_8$ alkyl. In one embodiment $R^9$ is a $C_2$-$C_6$ alkyl. In one embodiment $R^9$ is a $C_3$-$C_{12}$ alkyl. In one embodiment $R^9$ is a $C_3$-$C_{10}$ alkyl. In one embodiment $R^9$ is a $C_3$-$C_8$ alkyl. In one embodiment $R^9$ is a $C_3$-$C_6$ alkyl. In one embodiment $R^9$ is a $C_4$-$C_{12}$ alkyl. In one embodiment $R^9$ is a $C_4$-$C_{10}$ alkyl. In one embodiment $R^9$ is a $C_4$-$C_8$ alkyl. In one embodiment $R^9$ is a $C_4$-$C_6$ alkyl.

The "substituent pairs" recited herein refers to the two possible pyridyl substituents per one phthalo ring, wherein only one of the two is present. The substituents $R^1$-$R^8$ in the Formula I may be a pyridine or its N-alkylated derivative, however in such way that only one of the substituents of substituent pair $R^1$ and $R^2$, substituent pair $R^3$ and $R^4$, substituent pair $R^5$ and $R^6$, and substituent pair $R^7$ and $R^8$, is a pyridine or its alkylated derivative, and the other one is a hydrogen, i.e. not actually a substituent. The preparation method of the phthalocyanine of the embodiments yields a mixture of isomers wherein the pyridyl substituent may be on either isomeric position of the phthalo ring at the each four positions in the molecule of Formula I, and the pyridyl substituent is the same in all the substituent pairs. Representative examples of these molecules are shown in the following and in the FIGS. 4-7, wherein the substituents are presented at the same isomeric position of each of the four phthalo rings (for example corresponding to $R^1$, $R^3$, $R^5$ and $R^7$).

In one embodiment the phthalocyanine is a tetrakis[α-pyridyl] phthalocyanine of Formula II (Pc1):

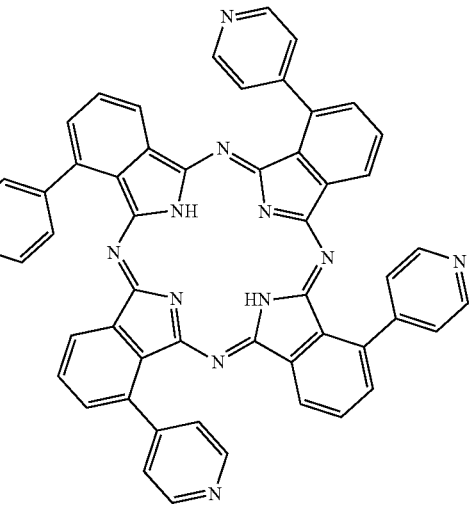

Formula II

The systematic name of this molecule is 1(4),8(11),15(18),22(25)-tetra(pyridin-4-yl)-29H,31H-phthalocyanine. The numbers in parenthesis represent the alternative positions of the substituents.

In one embodiment the phthalocyanine is a tetrakis[α-pyridyl] zinc phthalocyanine of Formula III (Pc2):

Formula III

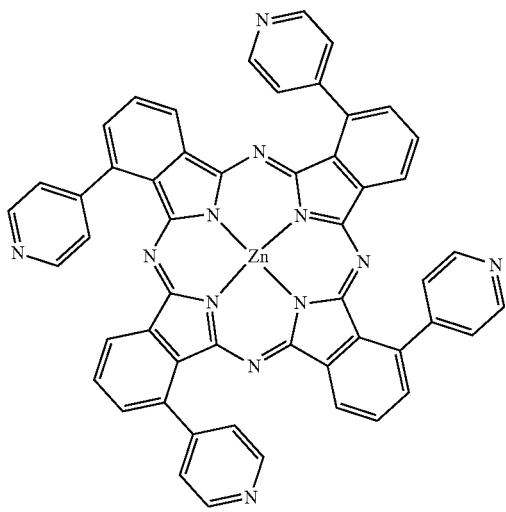

The systematic name of this molecule is [1(4),8(11),15(18),22(25)-tetra(pyridin-4-yl)-29H,31H-phthalocyaninato(2-)-κ4N29, N30, N31, N32]zinc. The numbers in parenthesis represent the alternative positions of the substituents.

In one embodiment the phthalocyanine is a tetrakis[m-ethyl α-pyridyl iodonium salt] phthalocyanine of Formula IV (Pc3):

Formula IV

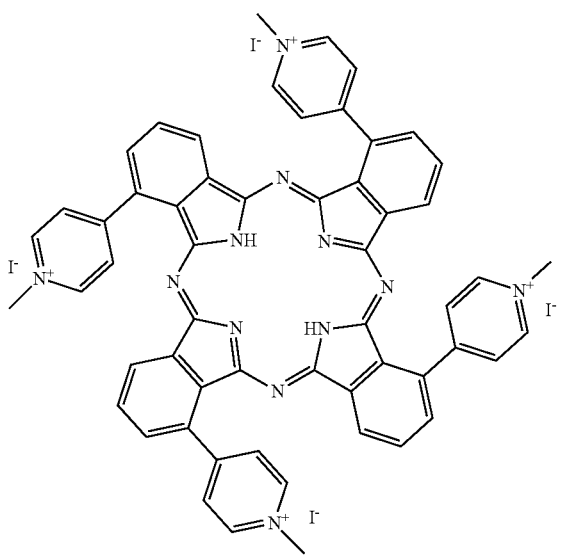

The phthalocyanine may be provided also in a form of another salt. Instead of iodonium also other counter ions may be provided, such as chloride, tosylate, bromine, sulfate, hexafluorophoshate, and the like.

The systematic name of this molecule is 4,4',4'',4'''-(29H,31H-phthalocyanine-1(4),8(11),15(18),22(25)-tetrayl)tetrakis(1-methylpyridinium) tetraiodide. The numbers in parenthesis represent the alternative positions of the substituents.

In one embodiment the phthalocyanine is a tetrakis[m-ethyl α-pyridyl iodonium salt] zinc phthalocyanine of Formula V (Pc4):

Formula V

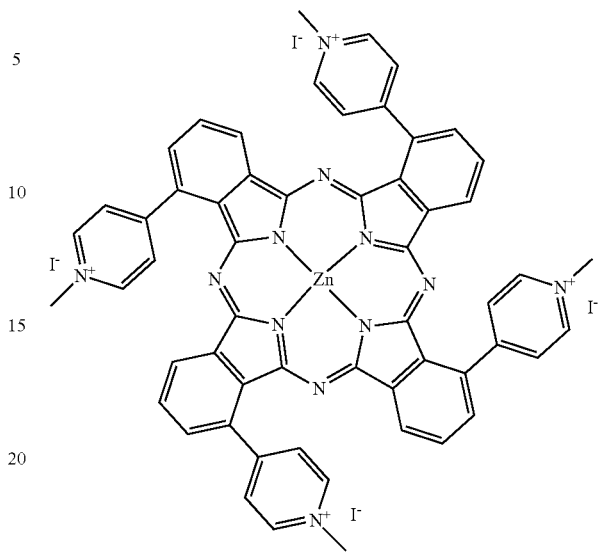

The systematic name of this molecule is {4,4',4'',4'''-(29H,31H-phthalocyanine-1(4),8(11),15(18),22(25)-tetrayl-κ 4N29,N30,N31,N32)tetrakis [1-methylpyridiniumato(2-)]}zinc(4+) tetraiodide. The numbers in parenthesis represent the alternative positions of the substituents.

The phthalocyanines of the embodiments have efficient photocatalytic properties, especially photosensitizer properties, which may be applied to a variety of different applications.

The phthalocyanine of the embodiments may be used for disinfecting materials, i.e. to kill microbes by releasing reactive oxygen species. For example it may be used to cover or impregnate a solid substrate and, upon illumination with light, the phthalocyanine dye inactivates the bacteria which come into a close distance to the surface. "Inactivate" means that the amount of colony forming units of the bacteria decreases.

The present disclosure provides solid materials, surfaces of which are self-disinfecting or self-sterilizing under light, especially visible light, by covering a solid substrate with the aforementioned phthalocyanine dye. Materials impregnated with the phthalocyanines may exhibit disinfecting or sterilizing properties throughout the material. The present disclosure also provides methods for preparing such materials.

Especially the antimicrobial activity of Pc4 is comparable with or superior to the best results of photodynamic inactivation of microorganisms published so far.

The alpha-pyridyl-substituted phthalocyanines Pc1-Pc4 described herein demonstrate high efficiency in photodynamic inactivation of bacteria. Especially Pc4 also demonstrates high stability as a dye for paper materials, and once impregnated to paper, does not release back to solution. Back release is a problem in many other substances used for preparation of antimicrobial surfaces.

The phthalocyanines of the embodiments can be used in coatings, walls, metal surfaces, ceramic tiles or other products, constructions or internal and external surfaces, for example as a dye molecule. The phthalocyanines Pc1-Pc4 can be used in filter materials for disinfection of gases (e.g. air in ventilation systems) or liquids (e.g. drinking water, hospital sewages, industrial or municipal or private wastewaters).

One embodiment provides an object coated or impregnated with the phthalocyanine of the embodiments. The object may be called as sterilizable or disinfectable object.

In one embodiment the object is selected from objects comprising fibrous material, such as a paper, a filter, a textile or a fabric; porous material; a wall; a glass surface; metal, such as a metal surface; plastic, such as a plastic surface; and ceramic material, such as a ceramic surface or porous ceramic material, for example a ceramic tile. In general textile may be also called as a fabric or cloth. The fabric may be woven or nonwoven. In case of clothes, the fabric is usually woven. More particularly, textile refers to any material made of interlacing fibers. Fabric refers to any material made through weaving, knitting, spreading, crocheting, or bonding that may be used in production of further goods (garments, etc.). A filter may contain fibrous material, such as paper or textile. The filter may be air filter or liquid filter, wherein the air or the liquid is arranged to flow through the filter. Fibrous material, as used in this disclosure, may comprise natural or synthetic fibers, or a combination thereof. Examples of natural fibers include fibers from plant, animal and mineral sources, such as cellulosic fibers. Examples of synthetic fibers include nylon, acrylic, polyester, rayon, glass and metallic fibers.

Plastic as used herein refers to synthetic or semi-synthetic organic compounds that are malleable and can be molded into solid objects. Plastics are generally organic polymers of high molecular mass, such as thermoplastic or thermosetting polymers, but they may also contain other substances. Examples of plastics include polyester, polyethylene terephthalate, polyethylene, high-density polyethylene, polyvinyl chloride, polyvinylidene chloride, low-density polyethylene, polypropylene, polystyrene, high impact polystyrene, polyamide, acrylonitrile butadiene styrene, polyethylene/acrylonitrile butadiene styrene, polycarbonate, polycarbonate/acrylonitrile butadiene styrene, polyurethane, maleimide/bismaleimide, melamine formaldehyde, plastarch material, phenol formaldehydes, polyepoxide, polyetheretherketone, polyetherimide, polyimide, polylactic acid, polymethyl methacrylate, polytetrafluoroethylene (Teflon), urea-formaldehyde, furan, silicone, and polysulfone.

Also beads, granules, microparticles and the like spherical or globular objects may be coated, impregnated or conjugated with the phthalocyanine of the embodiments. Examples of such beads include glass beads, plastic beads, ceramic beads. The beads, granules, microparticles and the like spherical or globular objects may be porous.

One group of objects include nanoparticles including nanoclusters, nanopowders, nanocrystals and nanorods, which may be used as stabilizer and delivery vehicles for photosensitizers, for example in PDT. Nanoparticles are particles with characteristic size less than 100 nm, in general particles between 1 and 100 nanometers in size, for example 5-80 nanometers, such as mean outer diameter or at least one dimension. Examples of nanoparticles include gold nanoparticles, silica nanoparticles, polymeric nanoparticles, such as synthetic organic polymers, for example acrylates; magnetic nanoparticles, such as iron oxide nanoparticles; semiconductor nanoparticles, such as metal oxide semiconductor nanoparticles, for example titanium dioxide and zinc oxide nanoparticles, which are semiconductor nanocrystals that catalytically generate reactive oxygen species; quantum dots, which are semiconductor nanocrystals, such as cadmium-selenide; and other nanoparticles. For example scintillation nanoparticles absorb ionizing radiation, such as X-rays or gamma rays, that can penetrate into human tissue deeper than UV or visible light. After absorption the scintillation nanoparticles become excited and radiate visible light, which will activate the photosensitizer in the tissue. Examples of scintillation nanoparticles include lanthanum fluoride nanoparticles, preferably doped with terbium ions. Also upconverting nanoparticles seek to overcome the limitation of light penetration through tissue by a mechanism wherein the upconverting nanoparticles are excited by near-infrared light, and the nanoparticles then emit light in the visible region of the spectrum to activate the photosensitizer in the tissue. Examples of upconverting nanoparticles include sodium yttrium fluoride nanoparticles co-doped with ytterbium and erbium ions. The nanoparticles may be used for example in therapeutic applications, such as in cancer therapy.

The objects disclosed in previous may be included in products for use in the applications described herein. Specific examples of the products include a self-disinfecting cloth, self-disinfecting fabrics for sanitary use (bed linen, etc), self-disinfecting protecting masks, and self-disinfecting filters for water. These are products of moderate activity and moderate price. Examples of larger-scale applications include disinfection filters for air-conditioning systems; self-cleaning surfaces for open water reservoirs and swimming pools; disinfection systems for hospital and other biohazardous waste waters.

Examples of products of moderate activity and lower price include self-disinfecting carpets and seats for kindergartens, public places, hospitals or households; self-disinfecting fabrics for seat covers and other surfaces in airplanes, buses, trains, cars; self-disinfecting tiles for water reservoirs, swimming pools, showers, toilet rooms; self-disinfecting disposable masks; self-disinfecting paints for walls; self-disinfecting filters for hospital wastewaters; and portable disinfection apparatus for drinking water.

Examples of products of high activity and high price include antimicrobial therapy medications for nasal and skin infections, wounds, ulcers; and dental treatment medications.

One embodiment provides a pharmaceutical composition comprising the phthalocyanine of the embodiments. The pharmaceutical composition may also comprise a pharmaceutically acceptable carrier, a vehicle, a filler, any additional agents, or a combination thereof. The composition may be aqueous or it may be provided in dry form. Such pharmaceutical compositions, which may be also called as medical compositions, may be provided as gels, suspensions, emulsions, liquids or the like form, which may be applied onto a skin, tooth, or other tissue, and also in cancer therapies into a tissue. The pharmaceutical composition may comprise any form of the phthalocyanine as described herein, such as coupled with nanoparticles or other objects.

Examples of products of high activity and low price include powders and disinfecting treatments for large land/water areas in epidemic regions.

The object may be coated or impregnated by using a coating, a paint or an impregnation composition comprising the phthalocyanine of the embodiments, i.e. by painting, such as by brushing, spraying, dipping, sizing, or otherwise applying the coating, the paint or the impregnation composition. The impregnation composition may be for example a solution, suspension, dispersion or emulsion, for example an aqueous solution, suspension, dispersion or emulsion.

One embodiment provides a coating comprising the phthalocyanine of the embodiments, preferably on an object. The coating may be prepared using methods known in the art, for example by using fibrous material or particulate material as a carrier. The carrier may be for example cellulosic material, such as nanofibrillar cellulose, which may be provided for example as powder. For example the filler may be mixed with the phthalocyanine dye, and then mixed with oil. A method for coating an object comprises forming a coating composition comprising the phthalocyanine of the embodiments and one or more carrier(s) and optionally other ingredients, and applying the coating composition onto the object to be coated. A method for impregnating an object comprises forming an impregnation composition comprising the phthalocyanine of the embodiments and one or more carrier(s) and optionally other ingredients, and impregnating the object to be impregnated with the impregnation composition.

In one example, as disclosed by Decraene et al in Curr Microbiol 2008 57: 269, light-activated antimicrobial coatings consisting of cellulose acetate (Sigma, Poole, UK) containing toluidine blue O (TBO; Sigma) and rose bengal (RB; Sigma) are prepared as follows. TBO and RB are added to solutions of cellulose acetate in acetone (50 mg/ml) to give a final concentration of 25 μm of each photosensitizer. Once completely dissolved, 3.5 ml of the cellulose acetate/photosensitizer solution are poured into small (diameter=50 mm) glass DUROPLAN® Petri dishes (Sigma) and the acetone is left to evaporate for 48 h. Control coatings consisting of cellulose acetate without the photosensitizers are prepared in a similar manner.

In another example the coatings are prepared as follows (Decraene et al. Appl. Environ. Microbiol. 2006, 72, 4436-4439). Cellulose acetate (Sigma) is dissolved in acetone (50 mg/ml), and stock solutions of the photosensitizers in acetone (100 g/ml) are added to give a final concentration of 25 M for each photosensitizer. Aliquots (450 1) of each mixture are transferred to flat-bottom glass containers (diameter, 18 mm), and the acetone is left to evaporate overnight. The thickness of the coatings is measured using a Starrett (Athol, Mass.) micrometer. The absorption spectrum of the coatings is determined using a UNICAM UV 500 UV/visible spectrophotometer (ThermoSpectronic) over the range 250 to 800 nm. A strong absorbance should occur between 500 nm and 675 nm, which includes three of the main emission peaks of the light source.

One embodiment provides a paint comprising the phthalocyanine of the embodiments, preferably on an object. The paint may be prepared using methods known in the art, for example by using a standard paint or coating composition as a carrier, such as transparent paint or coating composition.

In one example the paint is prepared as follows (Preuss et al, Journal of Photochemistry & Photobiology, B: Biology 2016 160 79-85). A commercially available standard silicone faced paint (StoColor Lotusan (Art. No. 03206-064)) is used to check the concept of photodynamic inactivation of biofilm building microorganisms. For the test a Lab formulation without added in-can preservatives are used in order to exclude influence from these substances. TMPyP is incorporated by gentle stirring with a Vollrath lab mixing equipment EXF for 1 min at 1500 U/min to yield a homogeneous distribution with a dynamic viscosity of 1.950 mPa s (20° C.). As positive control an identically formulated paint is used containing a concentration of active substances of dry-film biocides in the wet paint: 600 ppm Terbutryn (Cas No. 886-50-0), 1200 ppm Isoproturon (Cas No. 34123-59-6) and 1200 ppm IPBC (Cas No. 55406-53-6).

One embodiment provides a method for providing reactive oxygen species, the method comprising
  providing the phthalocyanine of the embodiments or the object described in previous, and
  irradiating the phthalocyanine or the object with light, to obtain reactive oxygen species.

In general a method for providing reactive oxygen species may be a therapeutic method or non-therapeutic method. In general the method for sterilizing of disinfecting materials are considered non-therapeutic. A therapeutic method is carried on a human or animal body. In one embodiment the method for providing reactive oxygen species is a non-therapeutic method.

The reactive oxygen species are chemically reactive chemical species containing oxygen. Examples of reactive oxygen species include e.g. peroxides (e.g. hydrogen peroxide $H_2O_2$), superoxide anion ($O_2^-$), superoxide radical ($O_2.$), hydroxyl radical (OH.) and singlet oxygen ($^1O_2$).

The light includes visible light, but also a part of UV-range and IR-range, such as light having a wavelength □ in the range of 350-850 nm, for example in the range of 400-800 nm. One wavelength optimum of the phthalocyanine molecule of the embodiments is in the range of 600-750 nm and one is at about 450 nm. The light may be natural light (sunlight) or it may be originated from one or more artificial light sources, such as a lamp, LED, laser or the like. In one example the method comprises providing a light source arranged to illuminate the phthalocyanine of the embodiments or the object described in previous.

In case of scintillation nanoparticles or upconverting nanoparticles or other similar materials also radiation or infrared light may be used for the irradiation as the irradiation will be converted into light with such wavelength that will activate the photosensitizer.

When the phthalocyanine of the embodiments or the object described in previous is irradiated with light, a photon is absorbed by the phthalocyanine i.e. the sensitizer. The absorbed photon excites the sensitizer to one or more energy-rich state(s). The excited sensitizer undergoes internal reactions that result in the chemical alteration of a substrate. This may occur in two types of reactions, namely Type-I and Type-II photoreactions, producing reactive oxygen species among others.

Type-I photoreactions are characterized by a dependence on the target-substrate concentration. In anoxic environments, the light induced excitation of the photosensitizer can promote an electron to a higher energy state. At this point a variety of reactions can take place. For example, this excited photosensitizer can react directly with organic substrates by electron exchange, filling the hole vacated by the excited electron, producing an oxidized substrate and reduced photosensitizer. Guanine, the most susceptible base to oxidation, is the presumed target leading to the formation of various oxo-guanine complexes and ultimately the decomposition of cellular DNA. The reduced photosensitizer can react with oxygen to produce superoxide anions ($O_2^-$) which can then form the highly reactive hydroxyl radical (OH.). The excited photosensitizer can also react with superoxide radicals ($O_2.$) to produce superoxide anions ($O_2^-$) which can then create the highly reactive hydroxyl radical (OH.).

The Type-II mechanism which is dependent on oxygen concentration also involves excitation of the photosensitizer with light, but in this mechanism energy is transferred to the ground state of molecular oxygen resulting in excited singlet oxygen ($^1O_2$) which goes on to destroy cellular function. The photosensitizer and oxygen interact through the triplet states because oxygen has a unique, triplet-ground state and low-lying excited states. The energy required for the triplet to singlet transition in oxygen is 22 kcal mol$^{-1}$ which corresponds to the energy of a wavelength of 1274 nm (infrared light). The energy needed to produce singlet oxygen is relatively low.

One embodiment provides a method for method for inactivating micro-organisms, comprising providing reactive oxygen species with the above method to inactivate the micro-organisms by oxidative action. The micro-organisms may be contained in the object containing the phthalocyanines of the embodiments, or in a material, which is in contact or in a close vicinity, such as 0-5 mm, with the object. For example the method may be used to inactivate micro-organisms on a surface or inside an object treated with the phthalocyanines of the embodiments, or in air or liquid, such as an aqueous liquid, passing the surface or the interior of the object, for example filter.

One embodiment provides a method for disinfecting materials, comprising providing reactive oxygen species with the above method to the material to disinfect the material by oxidative action. One embodiment provides a method for disinfecting a target, comprising providing reactive oxygen species with the above method to the target to disinfect the material by oxidative action. The target or the material may refer to a surface, air, liquid, such as water, aqueous liquid or other liquid, or a product such as the products described herein, which may be brought into contact with the reactive oxygen, or which may be used to further disinfect other targets, materials or substances. Disinfecting refers to an action of providing disinfecting or sterilizing effect in a target or a material, such as inactivating micro-organisms. Instead of the term "disinfecting" also the term "sterilizing" may be used. The reactive oxygen species may be considered as disinfecting or sterilizing agents.

One embodiment provides the use of the phthalocyanines of the embodiments for providing reactive oxygen species. One embodiment provides the use of the phthalocyanines of the embodiments for inactivating micro-organisms or disinfecting or sterilizing materials or targets, such as ones described herein.

The agents of the embodiments may be used in methods utilizing the principle of photodynamic inactivation (photoinactivation) or photodynamic antimicrobial chemotherapy, PACT. It employs a photosensitizer of the embodiments that generates, upon light irradiation, highly reactive species of singlet oxygen $^1O_2$, which in turn destroy the treated cells via oxidative action. This phototoxic effect has important advantages in antimicrobial treatments. Firstly, the lifetime of singlet oxygen is long enough to diffuse micrometers (in liquids) or even millimeters (in the air), thus allowing antimicrobial treatment on filters and even on biofilms without direct contact between a photosensitizer and a pathogen cell. It also enables the use of PACT materials in filters and bandages. Secondly, photoinactivation is a universal process and allows for treatment of various species of microorganisms simultaneously, also being efficient against multi-drug resistant (MDR) microbes. Thirdly, the phototoxic action is a general oxidation process and does not induce resistance compared to antimicrobial drugs.

The phthalocyanine of the embodiments may be used as a photosensitizer in photodynamic therapy (PDT), for example for treating cancer. One example of such cancer is melanoma, also called as skin cancer, which is further divided into three types of cancer: basal cell, squamous cell and melanoma. Basal cell and squamous cell cancers are the most common types of skin cancer, but they are less deadly and more readily treated than melanoma.

PDT may be use for treating numerous other health related conditions. For example, PDT may be used for treating immunological effects (new antibiotics), inflammation and bacterial infections. PDT activates and suppresses the immune system, by a combination of effects that begins after the light treatment. In cancer treatment the curative properties arise from the death of the irradiated cancer cells. The damage to the plasma membrane and membrane of the cellular organelles by singlet oxygen can trigger other events with far reaching consequences. PDT may be also used for treating dental infections, nasal infections, wounds, ulcers and the like.

Another PDT-induced effect is inflammation. Vascular destruction, observed after PDT, is similar to the inflammatory response after tissue injury or bacterial infection. Typical for this process is the release of a wide range of potent mediators including vasoactive substances, components of clotting cascades, proteinases, peroxidases, radicals, leucocytes, chemo attractants, cytokines, growth factors, and other immune regulators.

In photodynamic therapy in general a specific light source may be used, such as a medical laser system or other light source, which is equipped with optical fibres. The fibres may be inserted into a subject and the light may be directed to the target, such as to a tumour.

One embodiment provides a medical device containing the phthalocyanine of the embodiments, or the object described herein, such as a filter. One embodiment provides medical material, such as disinfecting substance such as a paste, a gel, an emulsion, a suspension, a liquid, a filter, a strip or the like, containing the phthalocyanine of the embodiments. One specific field of medical applications is dental applications and dentistry.

One embodiment provides the phthalocyanine of the embodiments for use as a therapeutic agent. One embodiment provides the phthalocyanine of the embodiments for use as a photosensitizer in photodynamic therapy, in general for treating diseases or disorders disclosed herein. One example provides a method for treating diseases or disorders, the method comprising providing the phthalocyanine of the embodiments as a photosensitizer in photodynamic therapy, and carrying out the photodynamic therapy for treating the diseases or disorders. Examples of the diseases include cancer, such as melanoma, esophageal cancer, non-small lung cancer, precancerous lesions, cancers of the brain, skin, prostate, cervix, and peritoneal cavity. The phthalocyanine of the embodiments may be provided as a pharmaceutical composition as described herein, for example coupled to particles, such as nanoparticles and/or in combination with one or more other pharmaceutical agent(s), such as anti-cancer agent(s).

One embodiment provides a 3-(pyridin-4-yl)benzene-1,2-dicarbonitrile. This is an intermediate compound which may be used for synthesising the phthalocyanines of the embodiments. The 3-(pyridin-4-yl)benzene-1,2-dicarbonitrile is represented by the formula VI:

Formula VI

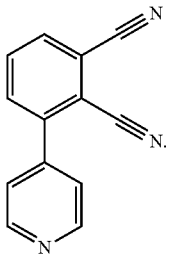

One embodiment provides a method for preparing 3-(pyridin-4-yl)benzene-1,2-dicarbonitrile, the method comprising
providing a mixture of pyridine boronate ester, triflate phthalonitrile, palladium catalyst, and $K_3PO_4$ in solution, such as dissolved in water and toluene, and heating and stirring, such as at a temperature in the range of 90-100° C., for example at about 90° C. for 1-3 h, for example about 2 h, and
recovering the 3-(pyridin-4-yl)benzene-1,2-dicarbonitrile from the solution.

One embodiment provides a method for preparing a phthalocyanine of Formula II,

Formula II

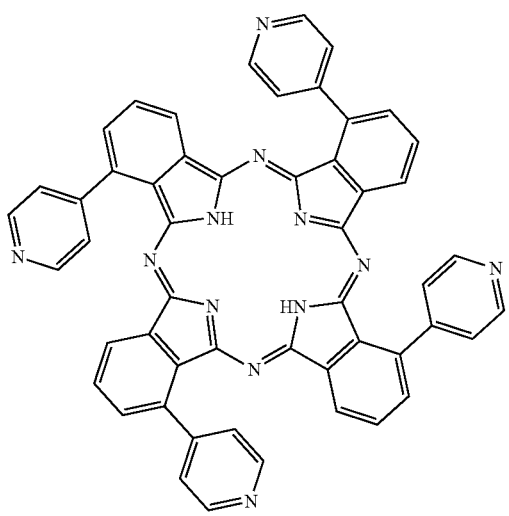

the method comprising
providing lithium dissolved in a solvent, preferably at a temperature in the range of 90-100° C., for example at about 90° C. under argon atmosphere,
cooling the mixture to room temperature,
adding 3-(pyridin-4-yl)benzene-1,2-dicarbonitrile, preferably under argon atmosphere
reacting at heating, such as at a temperature in the range of 90-100° C., for example at about 90° C., preferably in mixing, and
recovering the phthalocyanine of Formula II.

In one embodiment the method comprises
providing a mixture of the obtained phthalocyanine of Formula II and $Zn(OAc)_2 \cdot 2H_2O$ in a solvent, and
recovering the obtained tetrakis[α-pyridyl] zinc phthalocyanine of Formula III Formula III

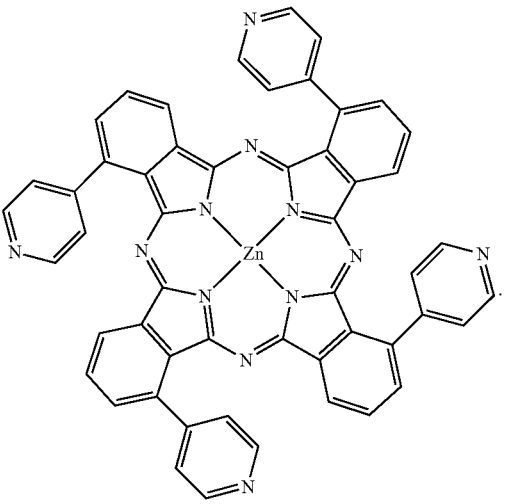

In one embodiment the method comprises
providing a mixture of the obtained phthalocyanine and methyl iodide in a solvent,
reacting the mixture at heating, such as at a temperature in the range of 40-60° C., for example at about 45° C. for 6-24 h, for example about 18 h,
cooling the mixture, and
recovering the obtained tetrakis[methyl α-pyridyl iodonium salt] phthalocyanine of Formula IV Formula IV

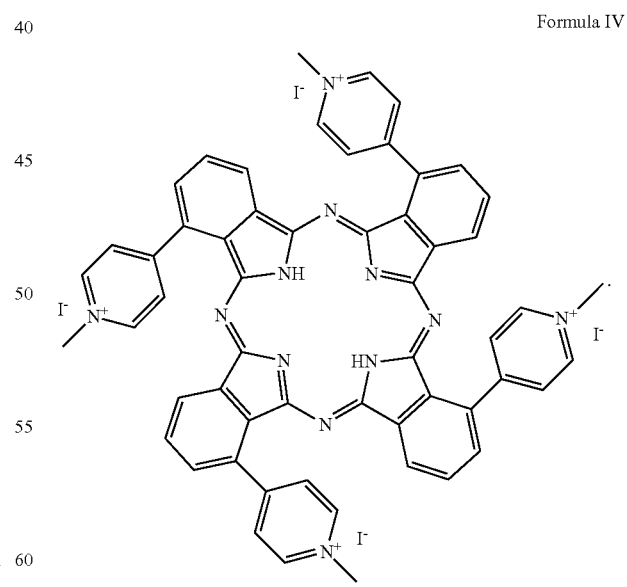

One embodiment provides a method for preparing a tetrakis[α-pyridyl] zinc phthalocyanine of Formula III, Formula III

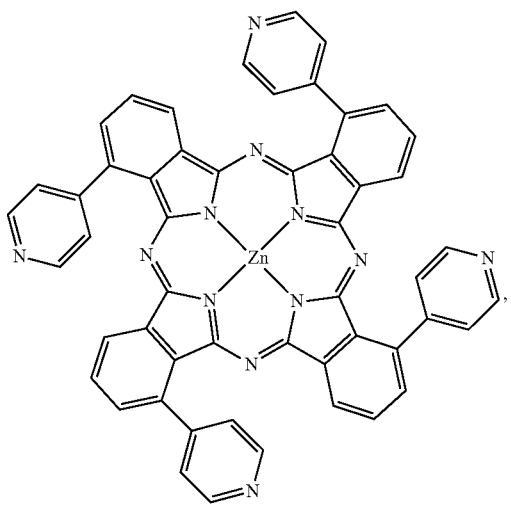

the method comprising
providing 3-(pyridin-4-yl)benzene-1,2-dicarbonitrile
heating the 3-(pyridin-4-yl)benzene-1,2-dicarbonitrile and zinc acetate in dimethylaminoethanol at reflux, such as at a temperature in the range of 120-150° C., for example at about 140° C. for 6-24 h, for example about 12 h,
cooling the mixture, and
recovering the obtained tetrakis[α-pyridyl] zinc phthalocyanine of Formula III.

In one embodiment the method comprises
providing a mixture of the obtained tetrakis[α-pyridyl] zinc phthalocyanine and methyl iodide in a solvent,
mixing at heating, such as at a temperature in the range of 40-60° C., for example at about 45° C. for 6-24 h, for example about 18 h,
cooling the mixture, and
recovering the obtained tetrakis[methyl α-pyridyl iodonium salt] zinc phthalocyanine of Formula V Formula V

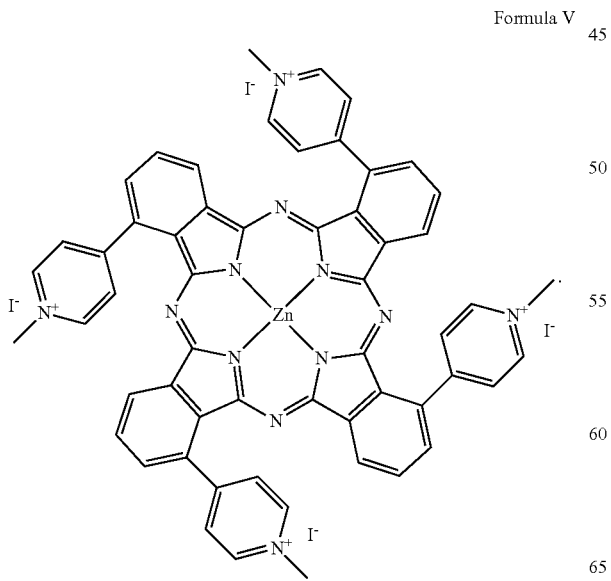

EXAMPLES

Example 1. Synthesis of Phthalocyanines Pc1-Pc4

1) 3-(Pyridin-4-yl)benzene-1,2-dicarbonitrile

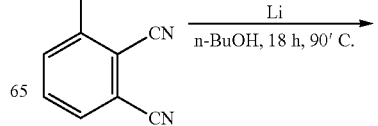

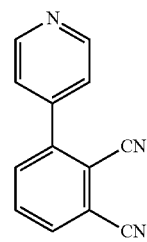

A mixture of pyridine boronate ester (120 mg, 0.628 mmol), Triflate phthalonitrile (173.5 mg, 0.628 mmol), PdCl$_2$(dppf).DCM (25.64 mg, 0.0314 mmol), K$_3$PO$_4$ (399.89 mg, 1.884 mmol) dissolved in 7.5 ml water and toluene (7.5 ml) were heated at 90° C. for 2 h. The product was extracted with CHCl$_3$ and washed with brine and dried over anhydrous Na$_2$SO$_4$ and evaporated under reduced pressure to get 105 mg of crude product. The pure product was isolated by re-precipitating with CHCl$_3$/hexane mixture (75 mg, 60%). The product 3-(pyridin-4-yl)benzene-1,2-dicarbonitrile may be also called as pyridine phthalonitrile or 3-pyridyl phthalonitrile.

2) Tetrakis[α-Pyridyl] phthalocyanine Pc1

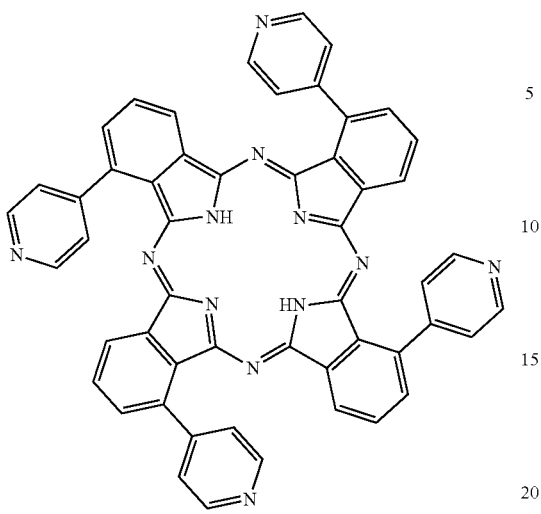

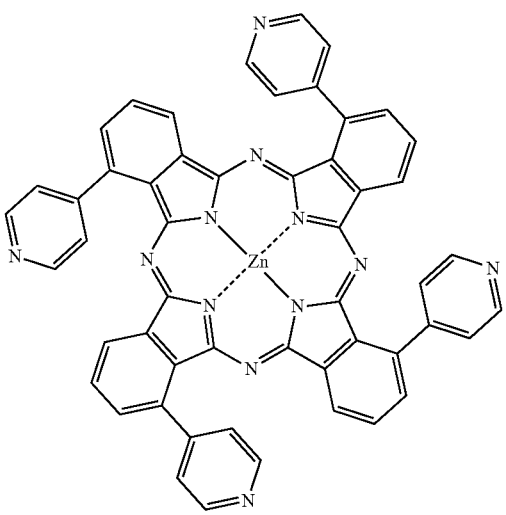

Freshly cut piece of lithium (57 mg, 8.212 mmol) was dissolved in n-butanol (5.7 ml) at 90° C. under argon atmosphere. The reaction mixture was allowed to cool to room temperature and pyridine phthalonitrile (80 mg, 0.3898 mmol) was added to the above solution under argon atmosphere. The temperature was increased to 90° C. and stirred for 18 h. The product was extracted with CHCl$_3$ and washed with water several times till the pH of the aqueous layer was neutral. The organic layer was evaporated under reduced pressure to get crude residue. The residue was washed with ACN and later purified by column chromatography (neutral alumina, 1% EtOH in CHCl$_3$) to get phthalocyanine free base (40 mg, 50%). MS (ESI-TOF): [M+H]$^+$ calcd for C$_{52}$H$_{30}$N$_{12}$$^+$, 823.2795; found, 823.2832.

Free base of pyridine phthalocyanine (12 mg, 0.0146 mmol) was dissolved in CHCl$_3$ (1.5 ml) and Zn(OAc)$_2$.2H$_2$O (12 mg, 0.0547 mmol) in 120 µl H$_2$O was added into it. The product was extracted with CHCl$_3$ (20 ml) and washed with water (25 ml×3), dried over anhydrous Na$_2$SO$_4$ and evaporated under reduced pressure to yield crude residue. The product was purified with column chromatography (neutral alumina, 10% EtOH in CHCl$_3$) and later washed with diethyl ether and ACN to get pure compound (11 mg, 85%). MS (ESI-TOF): [M+H]$^+$ calcd for C$_{52}$H$_{28}$N$_{12}$Zn$^+$, 885.1929; found, 885.1970.

3) Tetrakis[α-Pyridyl] Zinc Phthalocyanine Pc2

4) Tetrakis [Methyl α-Pyridyl Iodonium Salt] Phthalocyanine Pc3

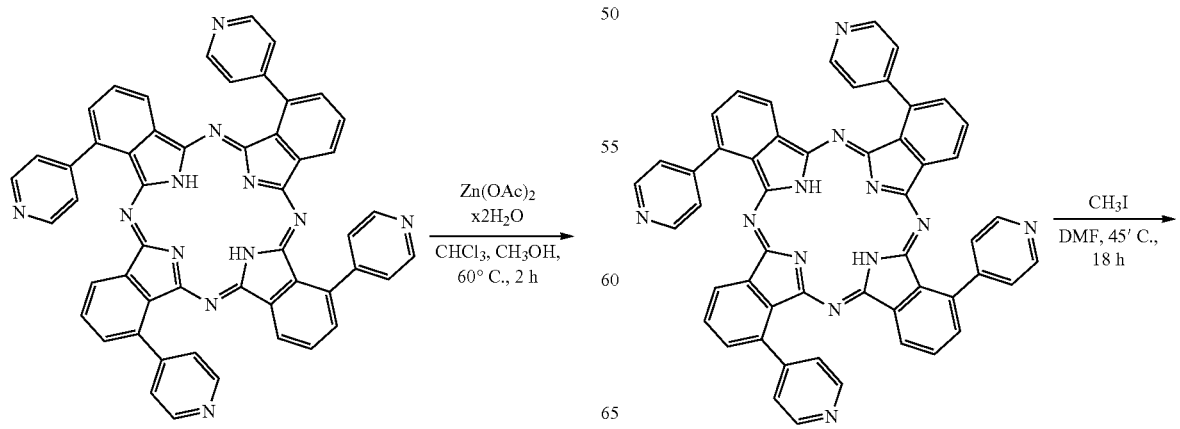

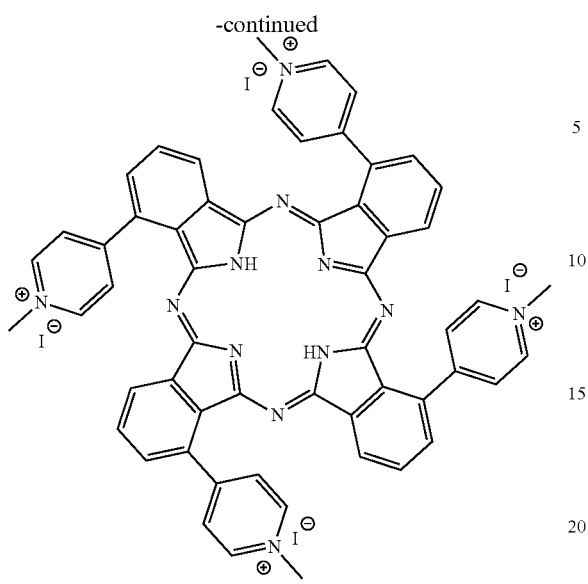

Free base of pyridine phthalocyanine (15 mg, 0.0182 mmol) was dissolved in DMF (3 ml) and methyl iodide (1 ml, 0.0161 mmol) was added into it. The reaction mixture was stirred at 45° C. for 18 h. The reaction mixture was cooled in an ice bath and product was precipitated by adding dimethyl ether (15 ml) into it. The solid filtered was washed several times with diethyl ether and later with acetone to get pure product (14.8 mg, 58.32%). MS (ESI-TOF): [M]$^{4+}$ calcd for $C_{56}H_{42}N_{12}^{4+}$, 220.5914; found, 220.5888; [M+I]$^{3+}$ calcd for $C_{56}H_{42}IN_{12}^{3+}$, 336.4233; found, 336.4203.

5) Tetrakis[α-Pyridyl] Zinc Phthalocyanine Pc2 (Direct Method)

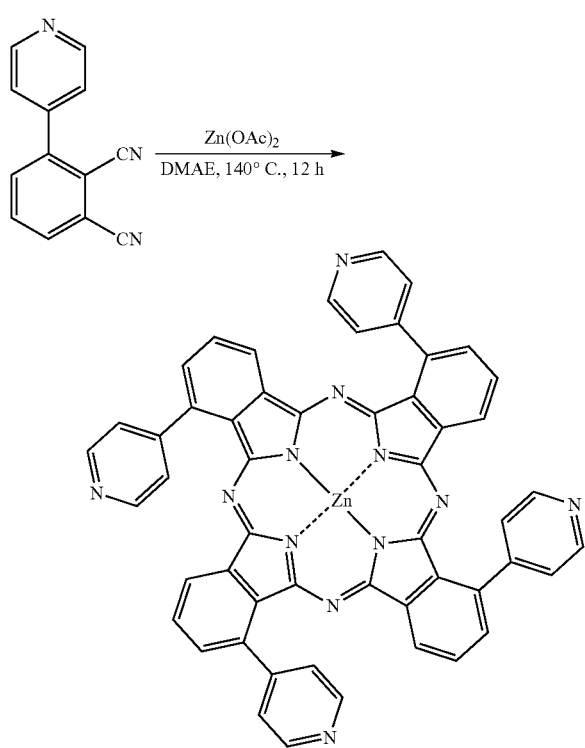

A mixture of pyridine phthalonitrile (77 mg, 0.3752 mmol) and zinc acetate Zn(OAc)$_2$(84.67 mg, 0.4615 mmol) in dimethylaminoethanol (DMAE, 810 µl) was heated at reflux at 140° C. for 12 h. The reaction mixture was cooled to room temperature and the product was precipitated by adding a mixture of MeOH/H$_2$O (9:1). The solid was filtered and washed with methanol to get pure product (80 mg, 96%). MS (ESI-TOF): [M+H]$^+$ calcd for $C_{52}H_{28}N_{12}Zn^+$, 885.1929; found, 885.1904.

6) Tetrakis[Methyl α-Pyridyl Iodonium Salt] Zinc Phthalocyanine Pc4

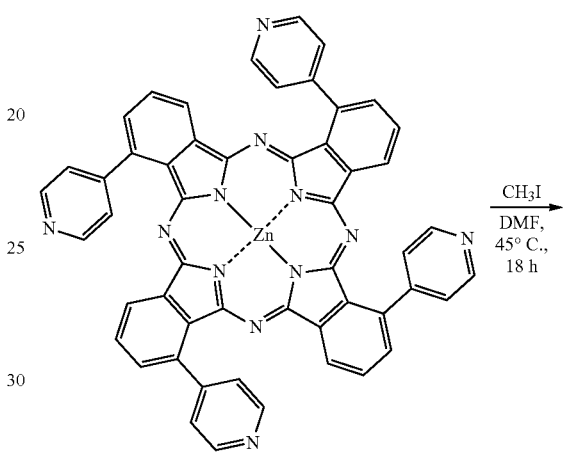

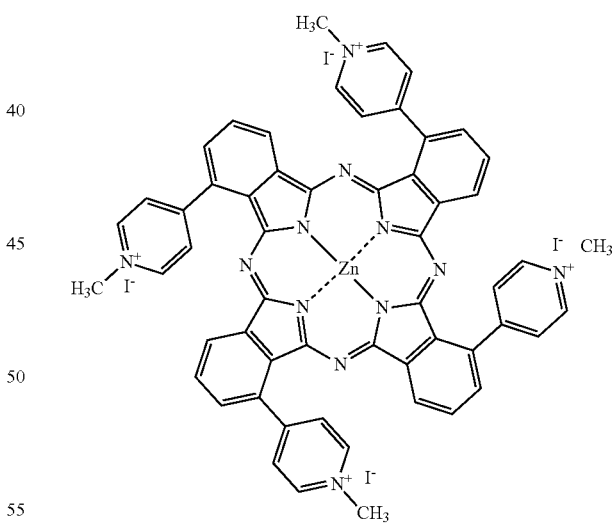

Pyridine phthalocyanine (20 mg, 0.0225 mmol) was dissolved in DMF (3 ml) and methyl iodide (1 ml, 0.0161 mmol) was added into it. The reaction mixture was stirred at 45° C. for 18 h. The reaction mixture was cooled in an ice bath and product was precipitated by adding diethyl ether (15 ml) into it. The solid filtered was washed several times with diethyl ether and later with mixture of acetone/H$_2$O (1:1) to get pure product (15 mg, 45.71%). MS (ESI-TOF): [M+I]$^{3+}$ calcd for $C_{56}H_{40}IN_{12}Zn^{3+}$, 357.0612; found, 357.0623.

Example 2. Antimicrobial Tests

Screening Test.

Figure 2:
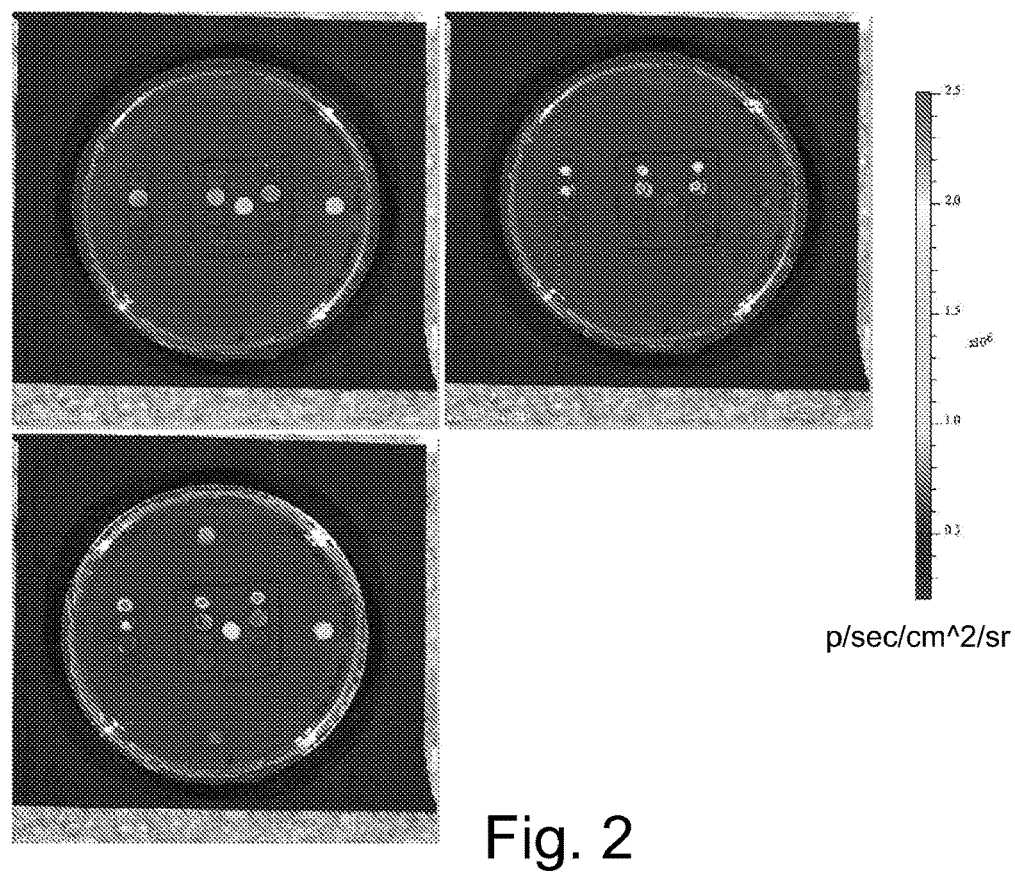
FIG. 2 shows a screening test with *Acinetobacterbaylyi* ADP1 carrying plasmid pBAV1C-T5-lux

The efficiency of dyes (Pc1, Pc2, Pc3, Pc4) was screened by conducting antimicrobial test with bioluminescent bacterial strains *Escherichia coli* (XL1-Blue, Stratagene, USA) and *Acinetobacter baylyi* ADP1 (DSM 24193) carrying plasmid pBAV1C-T5-lux (the plasmid is chloramphenicol resistance derivate of the pBAV1K-T5-lux plasmid (Addgene #55800). The filter papers (12.25 cm$^2$) were soaked in respective dye solution (0.9 mg dye in 200 μl solvent) and allowed to dry on it. After drying, three circular discs (0.5 cm diameter) were cut from each filter paper and pasted on the LA agar (15 g/l agar, 10 g/l tryptone, 5 g/l yeast extract, 5 g/l NaCl) gel plate in such a way that each row corresponds to each dye. A circular dark screen of 0.3 cm height with a square hole in the center was placed over the agar plate. The square hole was cut in such a way that, one column which includes all the four dyes will be under the dark area of the screen while the two remaining columns will be inside the square hole. Two filters [KG3 band pass filter (315-750 nm transmittance) and ЖC-17 yellow filter (transmittance >485 nm)] were placed over the square hole to remove the infrared and UV radiation. The whole setup was placed inside solar simulator (Luzchem, Canada) and the intensity of the illumination was adjusted to 18 mWcm$^{-2}$. Control sample to check the effect of dyes were prepared by cutting un-dyed filter paper of same size and placing under dark and illuminated areas of LA agar plate. Luminescence arising from the setup was recorded (Xenogen IVIS 100) before the microbial deposition on the filter paper discs. Microbial solution (5 μl) were pipetted over these filter paper discs and control sample to determine the influence of the filter paper on the growth of microbes were established by pipetting microbial solution on the dark region of the agar plate. Luminescence of the agar plate before and after illumination of 1 hour was measured and the efficient dye which produces less luminescence was screened out from the set. FIG. 1 shows the screening results with *E. coli* βBAV1C-T5-lux, and FIG. 2 shows the screening results with *Acinetobacter baylyi* ADP1 carrying plasmid βBAV1C-T5-lux.

Colony Forming Unit (CFU) Method.

Figure 3:
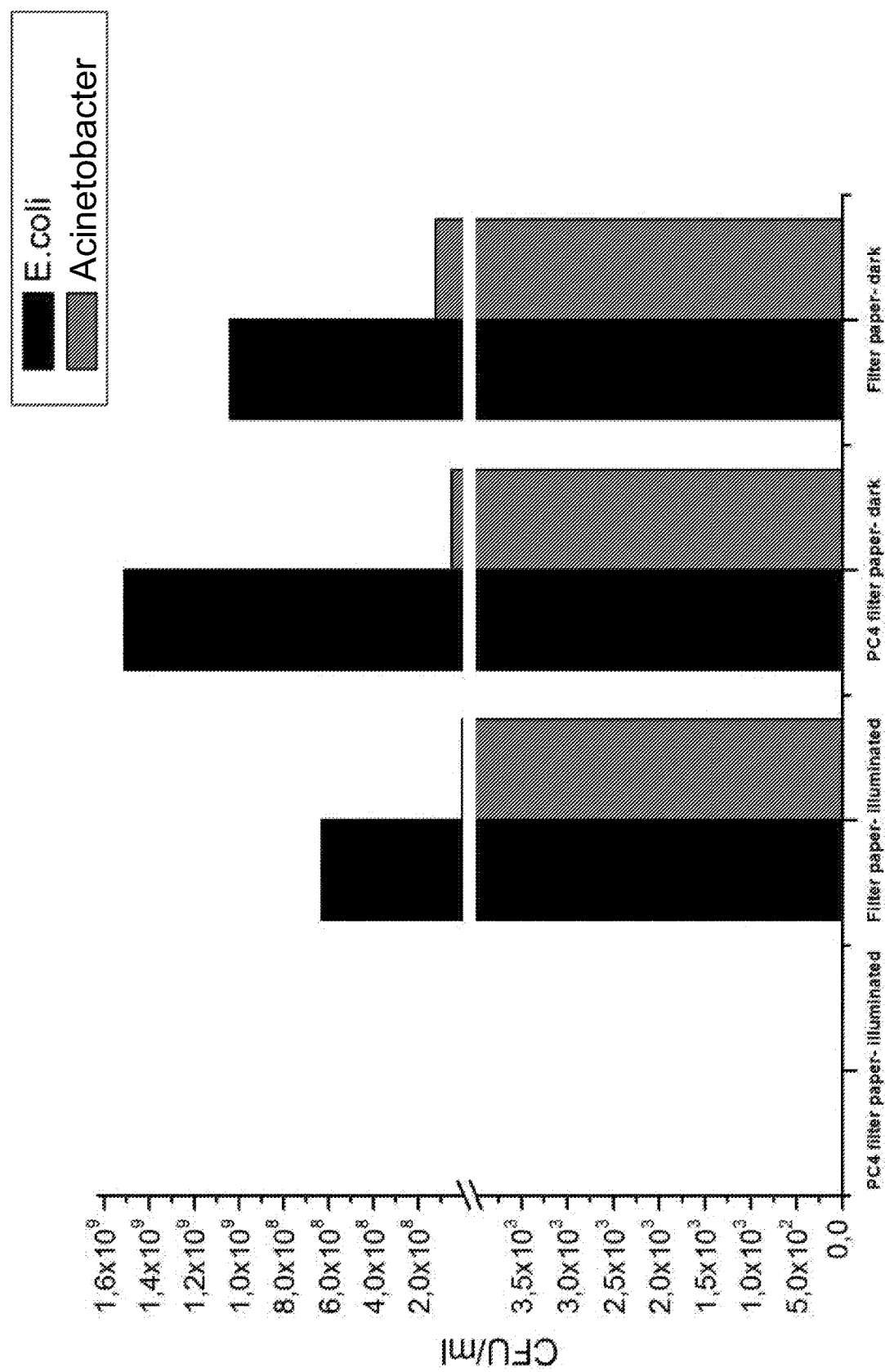
FIG. 3 shows a comparison of microbial growth in CFU/ml for illuminated Pc4 filter paper against control samples
Figure 4:
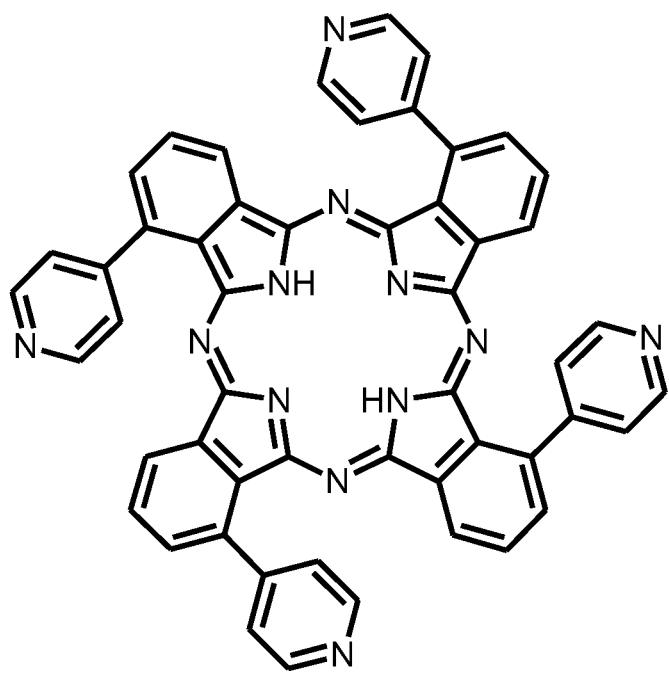
FIG. 4 shows a phthalocyanine of Formula II
Figure 5:
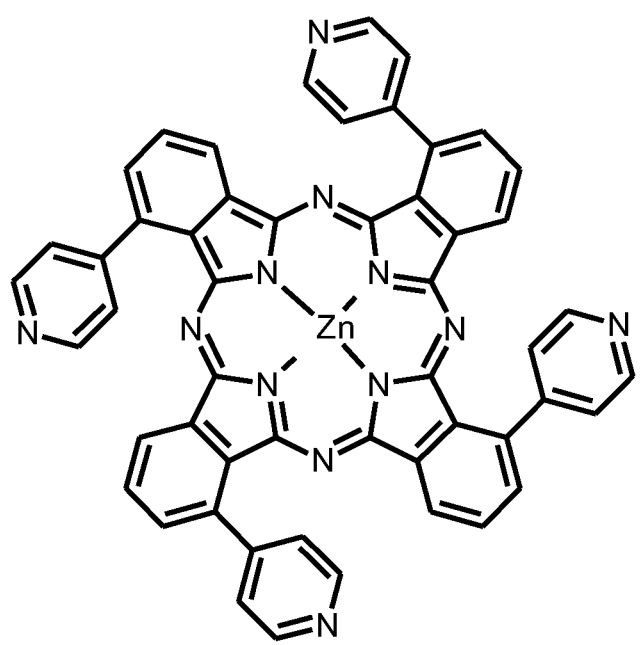
FIG. 5 shows a phthalocyanine of Formula III
Figure 6:
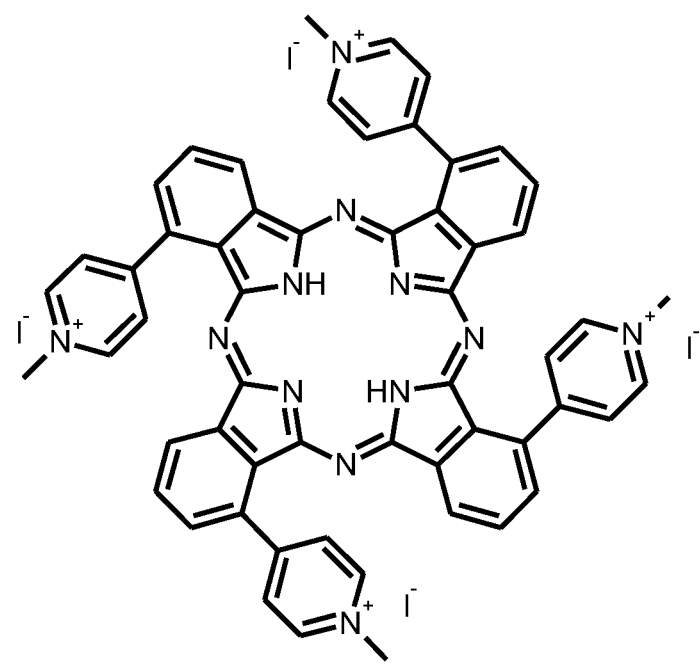
FIG. 6 shows a phthalocyanine of Formula IV
Figure 7:
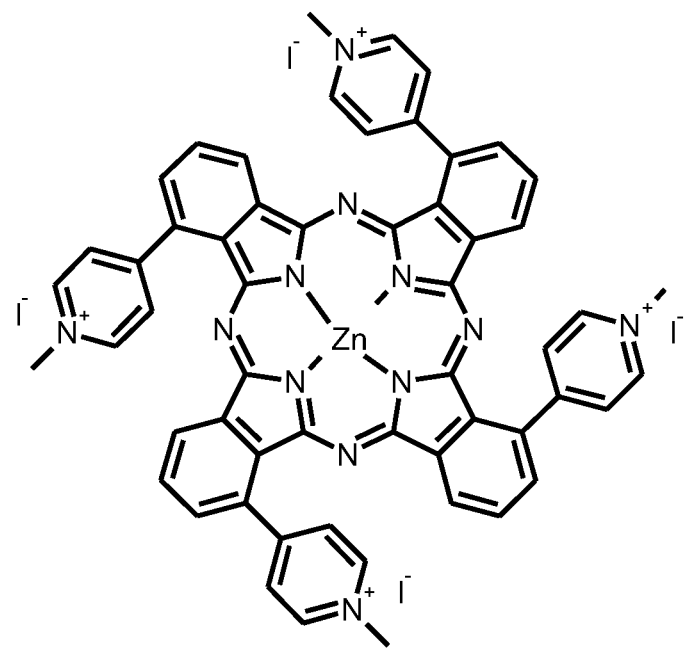
FIG. 7 shows a phthalocyanine of Formula V

The antimicrobial efficiency of the dye was confirmed by CFU method using microbes *E. coli* MG1655 (*E. coli* Genetic Resources at Yale) and *A. baylyi* ADP1 (ATCC 33305). Filter paper discs (original and duplicate) of the most efficient dye (Pc4) and un-dyed (dye control) filter paper were placed in the wells of microplate and microbial solution (25 μl) was pipetted over it. The microplate was illuminated in the solar simulator for 1 hour. UV-IR radiations were cut off using a combination of KG3 band pass filter (315-750 nm transmittance) and Жc-17 yellow filter (transmittance >485 nm). Similarly, light control samples were prepared by depositing microbial medium over dyed and un-dyed samples by covering microplate with aluminum foil for 1 h at room temperature. After 1 h of illumination or incubation, the microbes were extracted with LB medium (10 g/l tryptone, 5 g/l yeast extract, 5 g/l NaCl) (975 μl) and serial dilutions were made from each extract. The dilutions were then plated on LA agar plates and incubated at 30° C. overnight. The number of colonies grown on the agar plate was counted and CFUs per milliliter were calculated from it. No microbial growth (for *E. coli* and *A. baylyi*) were observed on the plates prepared from illuminated filter papers, while a growth of 10$^9$ and 10$^8$ CFU/ml for *E. coli* and *A. baylyi* respectively were observed on the plates prepared from control filter papers. This experiment clearly demonstrates the antimicrobial action of the filter paper treated with the dye Pc4 under light illumination, as summarized in Table 1 and FIG. 3.

TABLE 1

CFU counting results after photodynamic inactivation of bacteria with Pc4.

| Dilution | Dilution factor | Sample code | Sample code (Duplicate) | Volume of microbial solution plated (ml) | Colony counts after incubation | Colony counts after incubation (Duplicate) | Colony counts after incubation (Average) | CFU/ml |
|---|---|---|---|---|---|---|---|---|
| *E. Coli*/Illuminated Pc4 filter paper |||||||||
| 0.025 ml diluted to 1 ml | 2.50E−02 | I11 | I21 | 1.00E−01 | 0 | 0 | 0 | 0.00E+00 |
| 0.1 ml of above solution diluted to 1 ml | 2.50E−03 | I12 | I22 | 1.00E−01 | 0 | 0 | 0 | 0.00E+00 |
| 0.1 ml of above solution diluted to 1 ml | 2.50E−04 | I13 | I23 | 1.00E−01 | 0 | 0 | 0 | 0.00E+00 |
| 0.1 ml of above solution diluted to 1 ml | 2.50E−05 | I14 | I24 | 1.00E−01 | 0 | 0 | 0 | 0.00E+00 |
| 0.1 ml of above solution diluted to 1 ml | 2.50E−06 | I15 | I25 | 1.00E−01 | 0 | 0 | 0 | 0.00E+00 |
| *E. Coli*/Illuminated filter paper |||||||||
| 0.025 ml diluted to 1 ml | 2.50E−02 | B11 | B21 | 1.00E−01 | Too many to count | | | |
| 0.1 ml of above solution diluted to 1 ml | 2.50E−03 | B12 | B22 | 1.00E−01 | Too many to count | | | |
| 0.1 ml of above solution diluted to 1 ml | 2.50E−04 | B13 | B23 | 1.00E−01 | Too many to count | | | |
| 0.1 ml of above solution diluted to 1 ml | 2.50E−05 | B14 | B24 | 1.00E−01 | Too many to count | 584 | 548 | 2.19E+08 |
| 0.1 ml of above solution diluted to 1 ml | 2.50E−06 | B15 | B25 | 1.00E−01 | 316 | 0 | 158 | 6.32E+08 |

TABLE 1-continued

CFU counting results after photodynamic inactivation of bacteria with Pc4.

| Dilution | Dilution factor | Sample code | Sample code (Duplicate) | Volume of microbial solution plated (ml) | Colony counts after incubation | Colony counts after incubation (Duplicate) | Colony counts after incubation (Average) | CFU/ml |
|---|---|---|---|---|---|---|---|---|
| *E. Coli*/Pc4 filter paper-Dark ||||||||||
| 0.025 ml diluted to 1 ml | 2.50E−02 | P11 | P21 | 1.00E−01 | Too many to count | | | |
| 0.1 ml of above solution diluted to 1 ml | 2.50E−03 | P12 | P22 | 1.00E−01 | Too many to count | | | |
| 0.1 ml of above solution diluted to 1 ml | 2.50E−04 | P13 | P23 | 1.00E−01 | Too many to count | | | |
| 0.1 ml of above solution diluted to 1 ml | 2.50E−05 | P14 | P24 | 1.00E−01 | Too many to count | | | |
| 0.1 ml of above solution diluted to 1 ml | 2.50E−06 | P15 | P25 | 1.00E−01 | 327 | 429 | 378 | 1.51E+09 |
| *E. Coli*/Filter paper-Dark ||||||||||
| 0.025 ml diluted to 1 ml | 2.50E−02 | D11 | D21 | 1.00E−01 | Too many to count | | | |
| 0.1 ml of above solution diluted to 1 ml | 2.50E−03 | D12 | D22 | 1.00E−01 | Too many to count | | | |
| 0.1 ml of above solution diluted to 1 ml | 2.50E−04 | D13 | D23 | 1.00E−01 | Too many to count | | | |
| 0.1 ml of above solution diluted to 1 ml | 2.50E−05 | D14 | D24 | 1.00E−01 | Too many to count | | | |
| 0.1 ml of above solution diluted to 1 ml | 2.50E−06 | D15 | D25 | 1.00E−01 | 204 | 318 | 261 | 1.04E+09 |
| *Acinetobacter baylyi*/Illuminated Pc4 filter paper ||||||||||
| 0.025 ml diluted to 1 ml | 2.50E−02 | I11 | I21 | — | — | — | — | — |
| 0.1 ml of above solution diluted to 1 ml | 2.50E−03 | I12 | I22 | 1.00E−01 | 0 | 0 | 0 | 0.00E+00 |
| 0.1 ml of above solution diluted to 1 ml | 2.50E−04 | I13 | I23 | 1.00E−01 | 0 | 0 | 0 | 0.00E+00 |
| 0.1 ml of above solution diluted to 1 ml | 2.50E−05 | I14 | I24 | 1.00E−01 | 0 | 0 | 0 | 0.00E+00 |
| 0.1 ml of above solution diluted to 1 ml | 2.50E−06 | I15 | I25 | 1.00E−01 | 0 | 0 | 0 | 0.00E+00 |
| 0.1 ml of above solution diluted to 1 ml | 2.50E−07 | I16 | I26 | 1.00E−01 | 0 | 0 | 0 | 0.00E+00 |
| *Acinetobacter baylyi*/Illuminated filter paper ||||||||||
| 0.025 ml diluted to 1 ml | 2.50E−02 | B11 | B21 | — | — | — | — | — |
| 0.1 ml of above solution diluted to 1 ml | 2.50E−03 | B12 | B22 | 1.00E−01 | Too many to count | | | |
| 0.1 ml of above solution diluted to 1 ml | 2.50E−04 | B13 | B23 | 1.00E−01 | 332 | 307 | 319.5 | 1.28E+07 |
| 0.1 ml of above solution diluted to 1 ml | 2.50E−05 | B14 | B24 | 1.00E−01 | 32 | 38 | 35 | 1.40E+07 |
| 0.1 ml of above solution diluted to 1 ml | 2.50E−06 | B15 | B25 | 1.00E−01 | 1 | 3 | 2 | 8.00E+06 |
| 0.1 ml of above solution diluted to 1 ml | 2.50E−07 | B16 | B26 | 1.00E−01 | 2 | 0 | 1 | 4.00E+07 |
| *Acinetobacter baylyi*/Pc4 filter paper-Dark ||||||||||
| 0.025 ml diluted to 1 ml | 2.50E−02 | P11 | P21 | | | | | |
| 0.1 ml of above solution diluted to 1 ml | 2.50E−03 | P12 | P22 | 1.00E−01 | Too many to count | | | |
| 0.1 ml of above solution diluted to 1 ml | 2.50E−04 | P13 | P23 | 1.00E−01 | Too many to count | | | |
| 0.1 ml of above solution diluted to 1 ml | 2.50E−05 | P14 | P24 | 1.00E−01 | 175 | 178 | 176.5 | 7.06E+07 |
| 0.1 ml of above solution diluted to 1 ml | 2.50E−06 | P15 | P25 | 1.00E−01 | 22 | 4 | 13 | 5.20E+07 |
| 0.1 ml of above solution diluted to 1 ml | 2.50E−07 | P16 | P26 | 1.00E−01 | 6 | 1 | 3.5 | 1.40E+08 |
| *Acinetobacter baylyi*/Filter paper-Dark ||||||||||
| 0.025 ml diluted to 1 ml | 2.50E−02 | D11 | D21 | | | | | |
| 0.1 ml of above solution diluted to 1 ml | 2.50E−03 | D12 | D22 | 1.00E−01 | Too many to count | | | |
| 0.1 ml of above solution diluted to 1 ml | 2.50E−04 | D13 | D23 | 1.00E−01 | Too many to count | | | |

TABLE 1-continued

CFU counting results after photodynamic inactivation of bacteria with Pc4.

| Dilution | Dilution factor | Sample code | Sample code (Duplicate) | Volume of microbial solution plated (ml) | Colony counts after incubation | Colony counts after incubation (Duplicate) | Colony counts after incubation (Average) | CFU/ml |
|---|---|---|---|---|---|---|---|---|
| 0.1 ml of above solution diluted to 1 ml | 2.50E−05 | D14 | D24 | 1.00E−01 | 328 | 218 | 273 | 1.09E+08 |
| 0.1 ml of above solution diluted to 1 ml | 2.50E−06 | D15 | D25 | 1.00E−01 | 43 | 20 | 31.5 | 1.26E+08 |
| 0.1 ml of above solution diluted to 1 ml | 2.50E−07 | D16 | D26 | 1.00E−01 | 2 | 4 | 3 | 1.20E+08 |

Example 3. Antimicrobial Activity Under Weak Indoor Light

Figure 8:
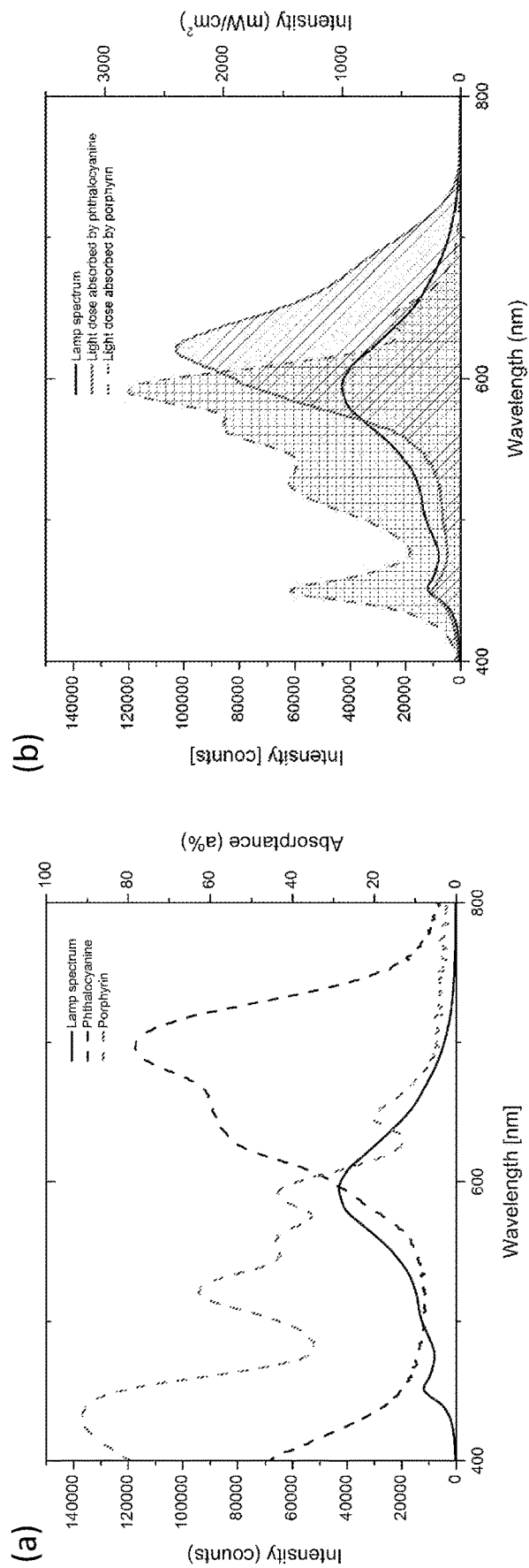
FIG. 8 shows the lamp profile and absorbance of the filter paper dyed with phthalocyanine Pc4 and porphyrin ZnPf
Figure 11:
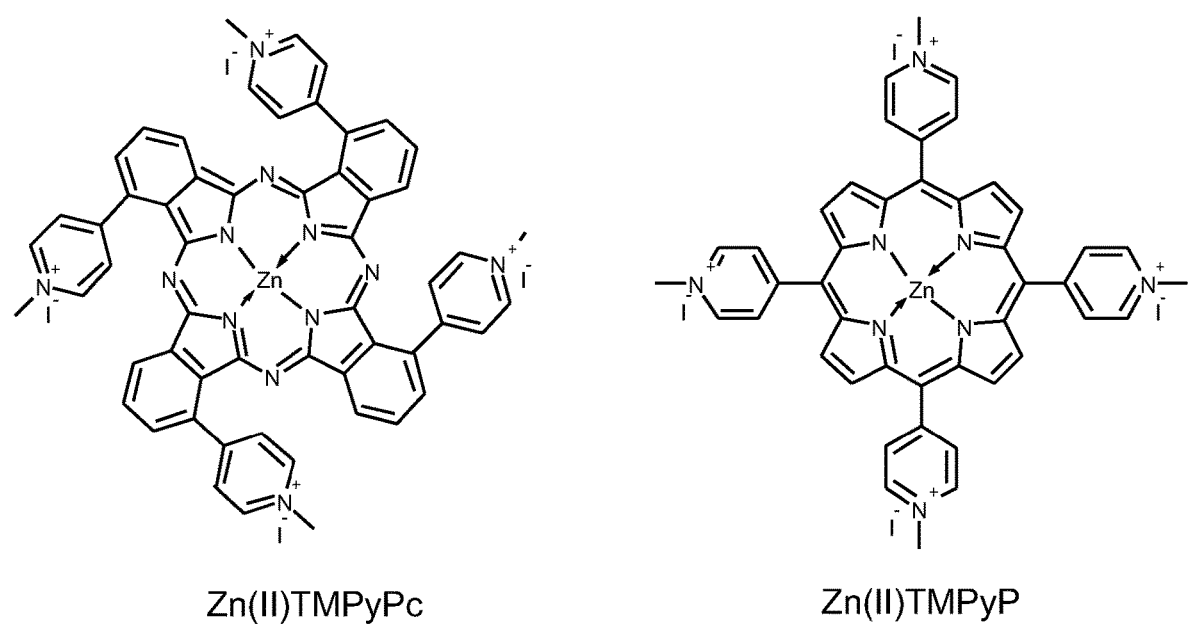
FIG. 11 shows the structures of Pc4 (Zn(II)TMPyPc) and the porphyrin ZnPf (Zn(II)TMPyP) used as a reference in tests.

It is demonstrated herein that dye Pc4 can be successfully activated by consumer-grade LED lamp (OSRAM LED Star PAR16 80 36° GU10, power consumption 6.9 W). The spectrum of light emitted from the lamp prior to the experiments was measured. The wavelength of lamp emission was found to be maximum at 594 nm (FIG. 8). In addition, the power density of the lamp was also measured at different distances. Intensities were found to be 4 mW/cm² at a distance 28 cm, 8 mW/cm² at 20 cm, 15 mW/cm² at 14 cm and 35 mW/cm² at distance 9 cm away from the detector. For comparison of activity one of the best known PACT photosensitizers, Zn(II)tetrakis[methylpyridinium iodide]porphyrin ZnPf (Zn(II)TMPyP) was used as a reference (structures presented in FIG. 11). Both Pc4 and ZnPf were deposited onto filter papers as described above. The absorptance of phthalocyanine Pc4 and porphyrin ZnPf papers were calculated from reflectance and transmittance measurement of dyed papers using integrating sphere (IS) detector. The absorptance profiles were very similar to the absorbance measurement in solution. Wavelength corresponding to the maximum absorption is 430 nm and 696 nm respectively for porphyrin and phthalocyanine. However, since two dyes absorb at two different wavelength, the light dose for each dye is different (FIG. 8b). The light dose for porphyrin is 1.2 times (5.2 J/cm²) higher than that of phthalocyanine (4.4 J/cm²) under same conditions using LED light. The antimicrobial inactivation experiments with illumination from LED lamp were conducted on *E. coli* and *A. baylyi* as described before. Both Pc4 and ZnPf demonstrated complete inactivation of microorganisms after 1 h illumination.

Example 4. Leeching Tests

Figure 9:
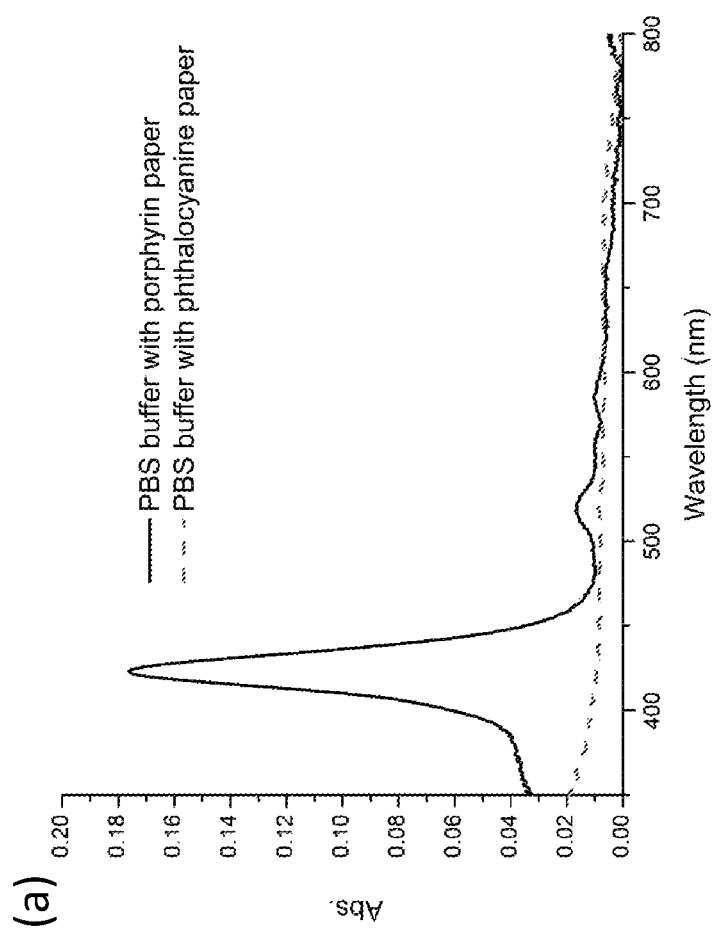
FIG. 9 shows (a) absorbance spectra and (b) emission spectra of PBS extracts of papers dyed with ZnPf and Pc4. Excitation wavelength was 422 nm for ZnPf and 694 nm for Pc4.
Figure 10:
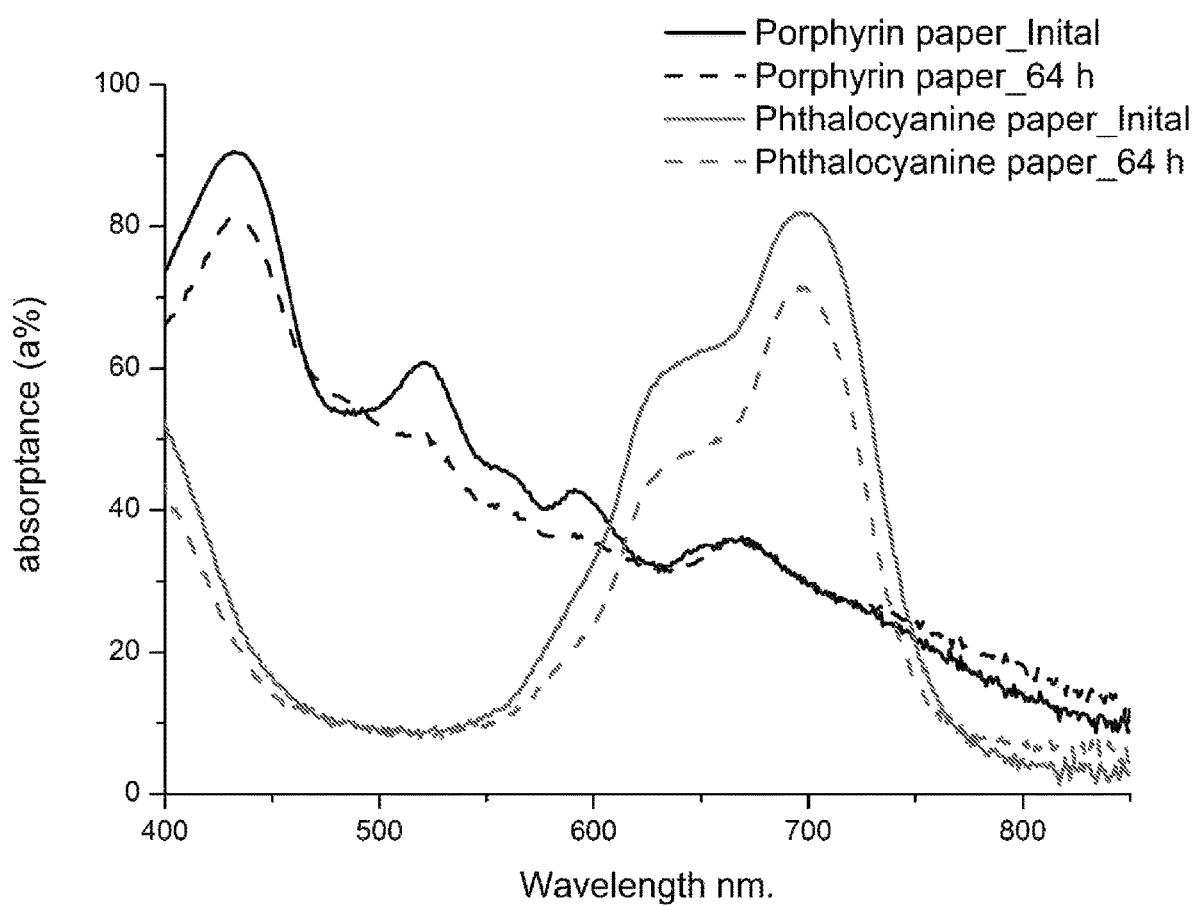
FIG. 10 shows absorptances (a %) of ZnPf dyed paper and Pc4 dyed paper against wavelength initially and after 64 hours.

Stability of the dye Pc4 against was tested with PBS buffer pH 7.2. The absorbance and emission of PBS buffer incubated with dye papers were measured for checking the leeching (FIGS. 9a and b). 28 mg of each dyed paper was soaked in 4 ml PBS buffer in a glass vial for 1 hour at room temperature. Absorbance and emission of PBS buffer from each vial was measured after 1 h to check the leeching of dyes from papers. The PBS solution with ZnPf showed a strong absorption peak at 422 nm which confirmed the leeching of porphyrin into the solution. The emission measurement of PBS solution with porphyrin paper excited at 422 nm displayed an intense emission peak from 600 nm after 1 hour of incubation. However, the PBS extract of Pc4 paper did not show any peak corresponding to the dye even after 20 h of incubation at room temperature. Upon excitation at 694 nm it however produced a very faint emission peak of negligible intensity. This shows that the dye Pc4 has exceptionally high stability against leeching, even though it is not chemically bound to cellulose support. FIG. 10 shows absorptances (a %) of porphyrin dyed paper and Pc4 dyed paper against wavelength initially and after 64 hours of constant illumination at 35 mW/cm².

The invention claimed is:

1. A phthalocyanine of Formula I:

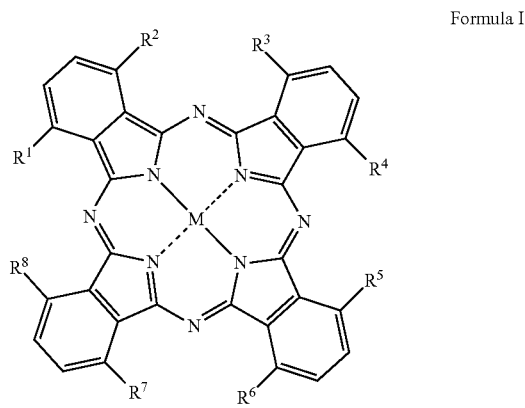

Formula I wherein M is a metal ion or two hydrogen atoms, and wherein the substituent pairs $R^1$ and $R^2$, $R^3$ and $R^4$, $R^5$ and $R^6$, and $R^7$ and $R^8$, independently of the other substituent pairs, are a hydrogen, and the other substituent is the same in all the substituent pairs and is selected from

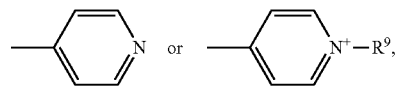

wherein $R^9$ is a $C_1$—$C_{18}$ is alkyl.

2. The phthalocyanine of claim 1 selected from the following:

the tetrakis[α-pyridyl] phthalocyanine of Formula II:

Formula II

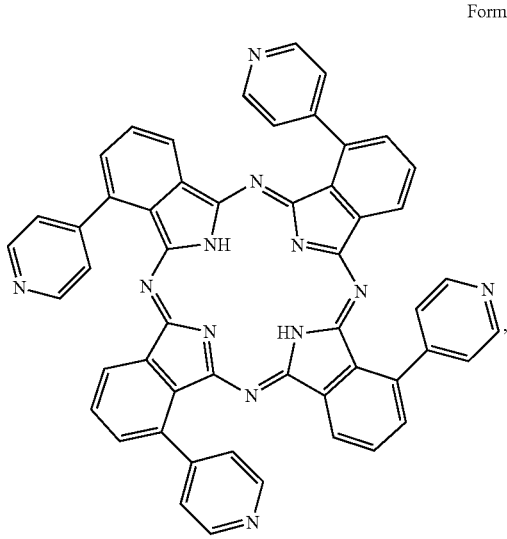

the tetrakis[α-pyridyl] zinc phthalocyanine of Formula III:

Formula III

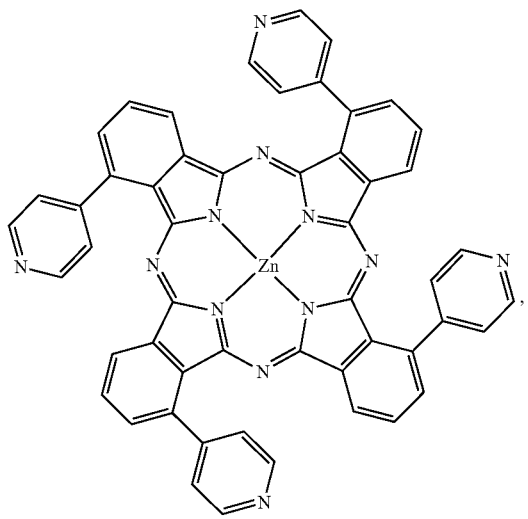

the tetrakis[methyl α-pyridyl iodonium salt] phthalocyanine of Formula IV:

Formula IV

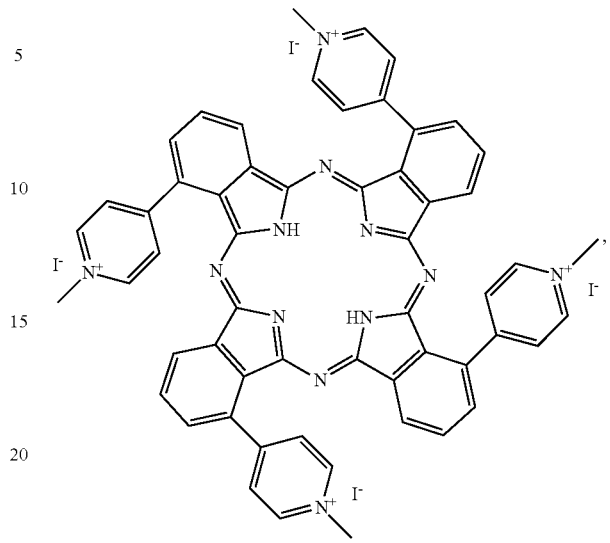

and
the tetrakis[methyl α-pyridyl iodonium salt] zinc phthalocyanine of Formula V:

Formula V

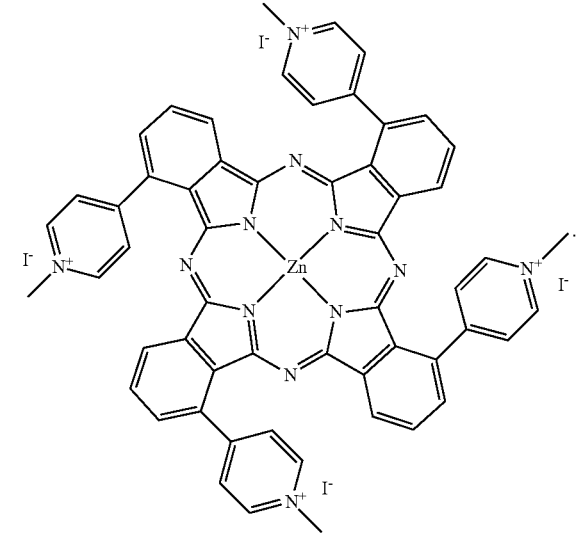

3. An object coated or impregnated with the phthalocyanine of claim 1, wherein the object is selected from objects comprising fibrous material, porous material; beads, granules, microparticles, nanoparticles; a wall; a glass surface; a metal surface; a plastic surface; and a ceramic surface.

4. A method for providing reactive oxygen species, the method comprising
providing the phthalocyanine of claim 1; and
irradiating the phthalocyanine or the object with light,
to obtain reactive oxygen species.

5. A method for inactivating micro-organisms, comprising providing reactive oxygen species with the method of claim 4 to inactivate the micro-organisms by oxidative action.

6. A method for providing reactive oxygen species, the method comprising providing an object coated or impregnated with the phthalocyanine of claim 1, wherein the object is selected from objects comprising fibrous material; porous material; beads, granules, microparticles, nanoparticles; a wall; a glass surface; a metal surface; a plastic surface; and a ceramic surface and irradiating the phthalocyanine or the object with light, to obtain reactive oxygen species.

7. A method for inactivating micro-organisms, comprising providing reactive oxygen species with the method of claim 6 to inactivate the micro-organisms by oxidative action.

8. 3-(Pyridin-4-yl)benzene-1,2-dicarbonitrile.

9. A method for preparing 3-(pyridin-4-yl)benzene-1,2-dicarbonitrile, the method comprising providing a mixture of pyridine boronate ester, triflate phthalonitrile, palladium catalyst, and K₃PO₄ in solution, heating and stirring, and recovering the 3-(pyridin-4-yl)benzene-1,2-dicarbonitrile from the solution.

10. A method for preparing a tetrakis[α-pyridyl] phthalocyanine of Formula II,

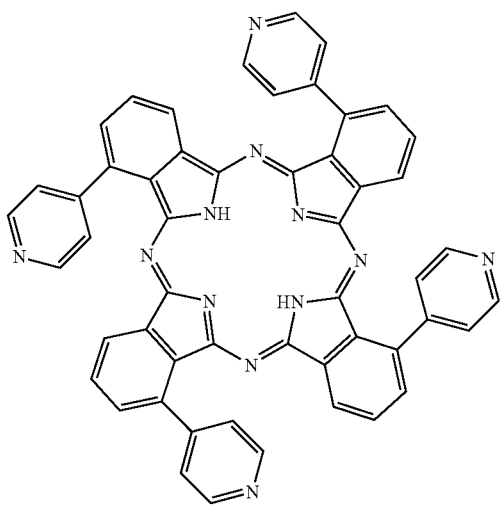

Formula II the method comprising providing lithium dissolved in a solvent, at a temperature in the range of 90-100° C. under argon atmosphere, cooling the mixture to room temperature, adding 3-(pyridin-4-yl)benzene-1,2-dicarbonitrile, reacting with heating, at a temperature of about 90-100° C., and recovering the obtained tetrakis[α-pyridyl] phthalocyanine of Formula II.

11. The method of claim 10, further comprising providing a mixture of the obtained phthalocyanine of Formula II and Zn(OAc)₂ ·2H₂O in a solvent, and recovering the obtained tetrakis[α-pyridyl] zinc phthalocyanine of Formula III

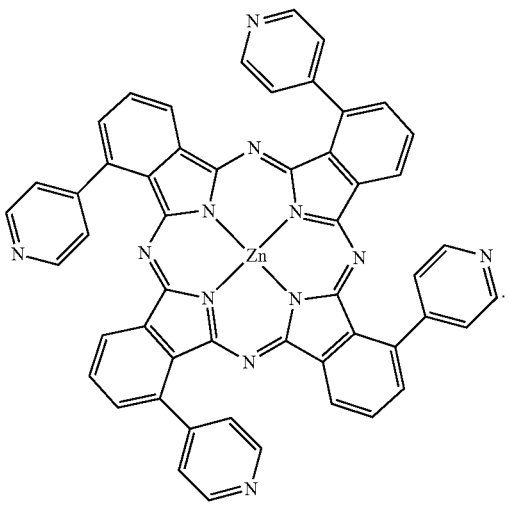

Formula III

12. The method of claim 11, further comprising providing a mixture of the obtained tetrakis[α-pyridyl] zinc phthalocyanine of Formula III and methyl iodide in a solvent, mixing at heating, at a temperature in the range of 40-60° C. for about 6-24 h, cooling the mixture, and recovering the obtained tetrakis[methyl α-pyridyl iodonium salt] zinc phthalocyanine of Formula V

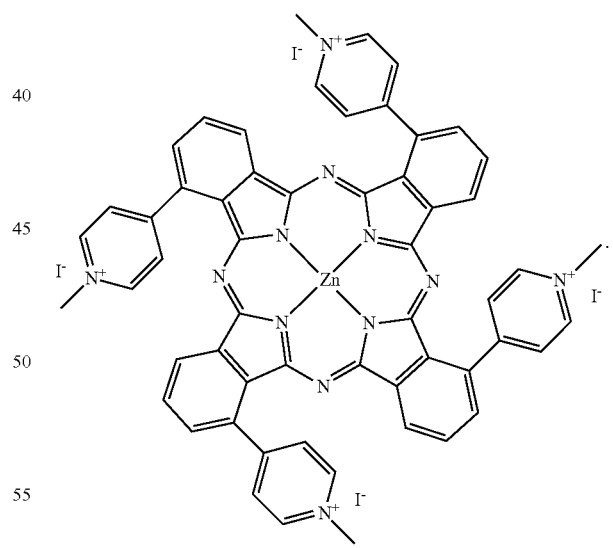

Formula V

13. The method of claim 10, further comprising providing a mixture of the obtained phthalocyanine and methyl iodide in a solvent, reacting the mixture at heating, at a temperature in the range of 40-60° C. for about 6-24 h, cooling the mixture, and recovering the obtained tetrakis [methyl α-pyridyl iodonium salt] phthalocyanine of Formula IV

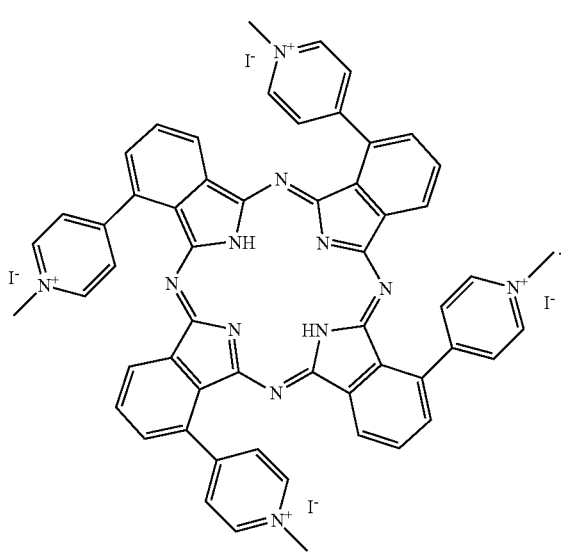

Formula IV

14. A method for preparing a tetrakis[α-pyridyl] zinc phthalocyanine of Formula III,

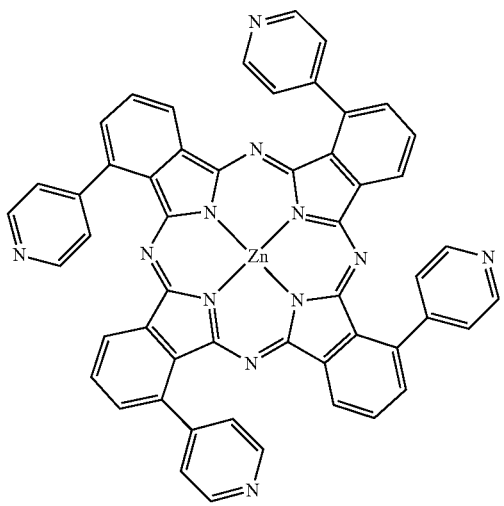

Formula III the method comprising
providing 3-(pyridin-4-yl)benzene-1,2-dicarbonitrile
heating the 3-(pyridin-4-yl)benzene-1,2-dicarbonitrile and zinc acetate in dimethylaminoethanol at reflux, at a temperature in the range of 120-150° C. for about 6-24 h,
cooling the mixture, and
recovering the obtained tetrakis[α-pyridyl] zinc phthalocyanine of Formula III.

15. The method of claim 14, further comprising
providing a mixture of the obtained tetrakis[α-pyridyl] zinc phthalocyanine and methyl iodide in a solvent, mixing at heating, at a temperature in the range of 40-60° C. for about 6-24 h,
cooling the mixture, and
recovering the obtained tetrakis[methyl α-pyridyl iodonium salt] zinc phthalocyanine of Formula V

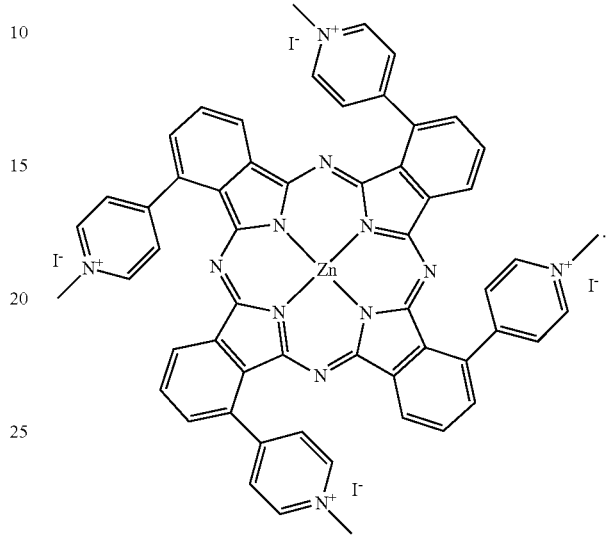

Formula V

16. A method for treating cancer, the method comprising providing the phthalocyanine of claim 1 as a photosensitizer in photodynamic therapy, and carrying out the photodynamic therapy for treating the cancer.

17. The method of claim 16, wherein the cancer is melanoma, esophageal cancer, non-small lung cancer, precancerous lesions, cancers of the brain, skin, prostate, cervix, and peritoneal cavity.

18. A method for treating cancer, the method comprising providing the coated or impregnated object of claim 3 as a photosensitizer in photodynamic therapy, and carrying out the photodynamic therapy for treating the cancer.

19. The method of claim 18, wherein the cancer is melanoma, esophageal cancer, non-small lung cancer, precancerous lesions, cancers of the brain, skin, prostate, cervix, and peritoneal cavity.

20. The method of claim 16, wherein the phthalocyanine is provided as a pharmaceutical composition.

21. The object of claim 3, wherein the fibrous material is a paper, a filter, a textile or a fabric.

22. The method for providing reactive oxygen species according to claim 6, wherein the fibrous material is a paper, a filter, a textile or a fabric.

23. The method of claim 16, wherein the phthalocyanine is provided as a pharmaceutical composition comprising the phthalocyanine coupled to particles.

24. The method of claim 16, wherein the phthalocyanine is provided as a pharmaceutical composition comprising the phthalocyanine in combination with at least one other pharmaceutical agent.

* * * * *